(12) United States Patent
Mak et al.

(10) Patent No.: US 6,552,246 B1
(45) Date of Patent: *Apr. 22, 2003

(54) TRANSGENIC MICE COMPRISING CD45 KNOCKOUT

(75) Inventors: Tak Wah Mak, Toronto (CA); Josef Martin Penninger, Toronto (CA)

(73) Assignee: University Health Network, Toronto (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/451,318

(22) Filed: May 26, 1995

Related U.S. Application Data

(60) Division of application No. 08/191,225, filed on Feb. 2, 1994, which is a continuation-in-part of application No. 08/067,767, filed on May 26, 1993, now abandoned.

(51) Int. Cl.⁷ ........................ A61K 67/027; C12N 15/00
(52) U.S. Cl. ................................. 800/18; 800/3; 800/25
(58) Field of Search .............................. 800/2, DIG. 1, 800/18, 3, 25; 435/172.3, 320.1; 424/9.2

(56) References Cited

FOREIGN PATENT DOCUMENTS

WO    WO 92/22645    12/1992

OTHER PUBLICATIONS

Gawin et al., Internet. Immunol. 2(2):173–180 (1990).*
Allan Bradley and Elizabeth Robertson, Embryo–Derived Stem Cells: A Tool for Elucidating the Developmental Genetics of the Mouse, *Current Topics in Developmental Biology*, vol. 20, pp. 357–371.
Chaffin et al., Dissection of thymocyte signaling pathways by in vivo expression of pertussis toxin ADP–ribosyltransferase: The EMBO Journal, vol. 9, No. 12, pp. 3821–3829, 1990.
Charbonneau et al., The leukocyte common antigen (CD45): A putative receptor–linked protein tyrosine phosphatase *Proc. Natl. Acad. Sci.*, vol. 85, pp. 7182–7186, Oct. 1988.
Ferrick et al., Transgenic Mice as an in vivo Model for Self–Reactivity, *Immunological Reviews*, No. 118, pp. 257–283, 1990.
Wai–Ping Fung–Leung and Tak Mak, Embryonic stem cells and homologous recombination, *Current Opinion Immunology*, 4: 189–194, 1992.
Fung–Leung et al., Immune Response against Lymphocytic Choriomeningitis Virus Infection in Mice without CD8 Expression, *J. Exp. Med.*, 174: 1425–1429, 1991.
Fung–Leung et al., CD8 Is Needed for Development of Cytotoxic T Cells but Not Helper T Cells, *Cell*, vol. 65, 443–449, 1991.

Johnson et al., Sequence Conservation in Potential Regulatory Regions of the Mouse and Human Leukocyte Common Antigen Gene, *The Journal of Biological Chemistry*, vol. 264, No. 11, pp. 6220–6229, 1989.
Joyner et al., Production of a mutation in mouse En–2 gene by homologous recombination in embryonic stem cells, *Nature*, vol. 338, pp. 153–156, 1989.
Justement et al., Regulation of B Cell Antigen Receptor Signal Transduction and Phosphorylation by CD45, *Science*, 252: pp. 1839–1842, 1991.
Kishihara et al., Normal B Lymphocyte Development but Impaired T Cell Maturation in CD45–Exon6 Protein Tyrosine Phosphatase–Deficient Mice, *Cell*, vol. 74, 143–156, Jul., 1993.
Koretzky et al., Tyrosine phosphatase CD45 is required for T–cell antigen receptor and CD2–mediated activation of a protein tyroine kinase and interleukin 2 production, *Proc. Natl. Acad. Sci.*, vol. 88, pp. 2037–2041, 1991.
Koretzky et al., Tyrosine phosphatase CD45 is essential for coupling T–cell antigen receptor to the phosphatidyl inositol pathway, *Nature*, vol. 346, pp. 66–68, Jul. 5, 1990.
Lee et al., The Genomic Organization of the CD28 Gene, *The Journal of Immunology*, vol. 145, 344–352, 1990.
Li et al., Human suppressor T cell clones lack CD28, *Eur. J. Immunol.*, 20: 1281–1288, 1990.
Peter S. Linsley and Jeffrey A. Ledbetter, The Role of the CD28 Receptor During T Cell Resesponses to Antigen, *Annu. Rev. Immunol.*, 11: 191–212, 1993.
Love et al., T Cell Development in Mice That Lack the ξ Chain of the T Cell Antigen Receptor Complex, *Science*, vol. 261 pp. 918–921, Aug., 1993.
Tak Mak et al., Generation of Mutant Mice Lacking Surface Expression of CD4 or CD8 By Gene Targeting, *Journal of Autoimmunity*,5: 55–59, 1992.
Molina et al., Peripheral T Cells in Mice Lacking p56lck Do Not Express Significant Antiviral Effector Functions 1, The Jouranl of Immunology, vol. 151, 699–706, No. 2, Jul. 1993.
Molina et al., Product block in thymocyte development in mice lacking p56lck, *Nature*, vol. 357, 161–164, 1992.
Penninger et al., Requirement for Tyrosine Kinase p56lck for Thymic Development of Transgenic γδ T Cells, *Science* vol. 260, 358–361, Apr., 1993.
Pfeffer et al., Mice Deficient for the 55 kd Tumor Necrosis Factor Receptor Are Resistant to Endotoxic Shock, yet Succumb to L. monocytogenes Infection, *Cell*, vol. 73, 457–467, May 1993.

(List continued on next page.)

*Primary Examiner*—Deborah Crouch
(74) *Attorney, Agent, or Firm*—Nancy A. Oleski; Steven M. Odre

(57) ABSTRACT

A mammal lacking expression of particular CD45 isoform in certain cells of the immune system is provided. The mammal may optionally contain a transgene encoding the CD45RO isoform. Also provided are methods of using these mammals.

4 Claims, 6 Drawing Sheets

OTHER PUBLICATIONS

Pingel and Thomas, Evidence That the Leukocyte–Common Antigen Is Required for Antigen–Induced T Lymphocyte Proliferation, *Cell*, vol. 58, 1055–1065, 1989.

Rahemtulla et al., Targeted disruption of the murine CD4 gene in the germ–line by homologous recombination, *INSERM*, vol. 219, 287–289, 1991.

Rahemtulla et al., Normal development and function of CD8+ cells but markedly decreased helper cell activity in mice lacking CD4, *Nature*, vol. 353, 180–184, 1991.

Schilham et al., Alloreactive cytotoxic T cells can develop and function in mice lacking both CD4 and CD8, *Eur. J. Immunol.*, 23: 1299–1304, 1993.

Shahinian et al., Differential T Cell Costimulatory Requirements in CD28–Deficient Mice, *Science*, vol. 261, pp. 609–612, Jul., 1993.

Matthew L. Thomas, The Leukocyte Common Antigen Family, *Annual Review of Immunology*, vol. 7, pp. 339–369, 1989.

Thomas and Capecchi, Site–Directed Mutagenesis by Gene Targeting in Mouse Embryo–Derived Stem Cells, *Cell*, vol. 51, pp. 503–512, 1987.

Thompson et al., Germ Line Transmission and Expression of a Corrected HPRT Gene Produced by Gene Targeting in Embryonic Stem Cells, *Cell*, vol. 56, pp. 313–321, 1989.

Trowbridge et al., CD45: a leukocyte–specific member of the protein tyrosine phosphatase family, *Biochimica et Biophysica Acta*, 1095, pp. 46–56, 1991.

Tonks et al., Demonstration That the Leukocyte Common Antigen CD45 is a Protein Tyrosine Phosphatase, *Biochemistry*, vol. 27, No. 24, pp. 8695–8701, 1988.

Wallace et al., CD45RA and CD45RB high Expression Induced by Thymic Selection Events, *J. Exp. Med.*, vol. 176, 1657–1663, 1992.

Weaver et al., CD8+ T–Cell Clones Deficient In the Expression of the CD45 Protein Tyrosine Phosphatase Have Impaired Responses to T–CellReceptor Stimuli, *Molecular and Cellular Biology*, vol. 11, No. 9, pp. 4415–4422, 1991.

Chui et al., Specific CD45 isoforms differentially regulate T cell receptor signaling, *The EMBO Journal*, vol. 13, No. 4, pp. 798–807, 1994.

Ong et al., Thymic CD45 Tyrosine Phosphatase Regulates Apoptosis and MHC–Restricted Negative Selection, *Journal of Immunology*, pp. 3793–3805, 1994.

Elliott et al., Targeted Gene Disruption of the Murine CD45 Gene in Embryonic Stem Cells, *J. of Cellular Biochemistry*, p. 208, supplement 15A, Jan. 10–24, 1991.

Holmes et al., Analysis of Complete and Partial Genetic Deficiencies of CD45 in Transgenic Mice, *J. of Cellular Biochemistry*, supplement 0 (18D), Keystone Symposium, Keystone Colorado, Apr. 10–17, 1994.

Ong et al., Activities of Specific CD45 Isoforms Expressed in Transgenic Mice, *J. of Cellular Biochemistry*, p. 197, supplement 0 (16 Part B), Keystone Symposium, Keystone, Colorado, Jan. 26–Feb. 2, 1992.

* cited by examiner

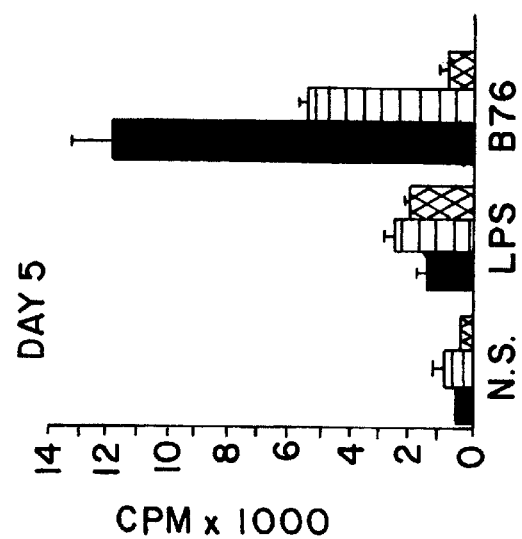
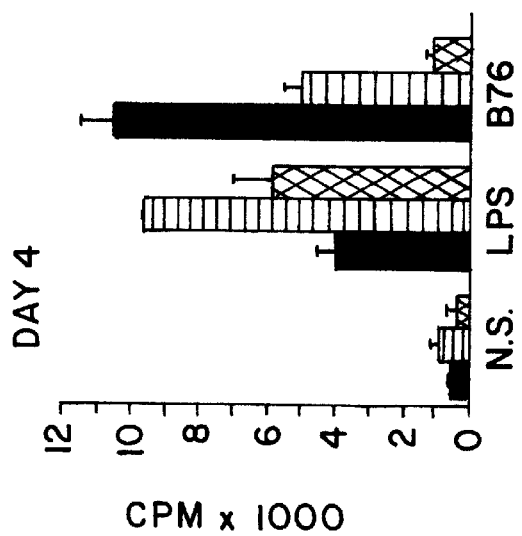
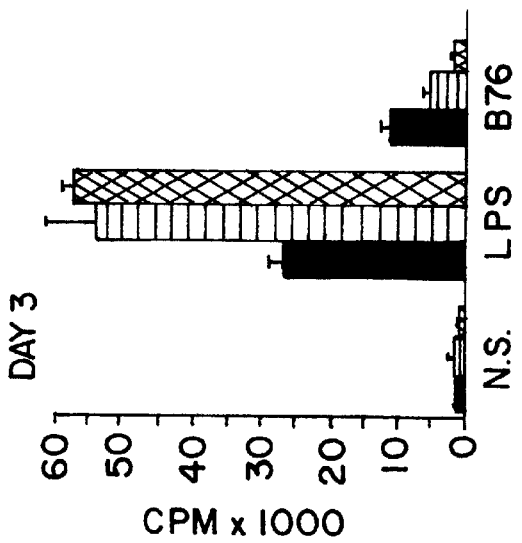

TRANSGENIC MICE COMPRISING CD45 KNOCKOUT

This application is a division, of application Ser. No. 08/191,225 filed Feb. 2, 1994 which is hereby incorporated by reference.

This application is a continuation-in part of U.S. Ser. No. 08/067,767 filed May 26, 1993, abandoned Aug. 6, 2002.

FIELD OF THE INVENTION

This invention relates to mammals in which the expression of one or more genes has been suppressed, and/or one or more genes have been inserted. More specifically, the invention concerns insertion of an exogenous DNA construct into the genomic DNA of mammals thereby producing transgenic mammals with decreased or completely suppressed expression of an endogenous gene or genes, and/or with expression of a novel gene or genes.

DESCRIPTION OF RELATED ART

The immune system of mammals is comprised of many specialized cells that act together in a highly complex and orchestrated manner to protect the mammal from invading pathogens, toxins, and other foreign substances.

Cells responsible for the specificity of the immune system are referred to as lymphocytes. Lymphocytes are a class of white blood cells. Two important classes of lymphocytes are T cells and B cells. T cells develop in the thymus, and are responsible for cell mediated immunity. There are many types of specialized T cells, such as for example, helper T cells (which enhance the activity of other types of white blood cells), suppressor T cells (which suppress the activity of other white blood cells), and cytotoxic T cells (which kill cells). B cells develop in the bone marrow and exert their effect by producing and secreting antibodies.

Many disorders of the immune system exist, and new disorders are continually identified. One type of commonly occurring immune disorder is the hyperactive immune system. Here, certain factors induce particular cell types in the immune system to become activated when they should not be.

Another type of immune disorder is auto immunity. This disorder is characterized by the immune system mounting an immune response against the mammal's own tissues.

Several proteins and other molecules have been identified as having key functions in regulating the immune system response of mammals. Two such proteins are CD28 and CD45.

CD28 receptor, also known as CD28, is a homodimer of molecular weight about 44 kilodaltons (kD). CD 28 is expressed at different levels on the cell surface of various T cells, and has a molecular structure similar to receptors of the immunoglobulin supergene family. CD28 appears to be involved in regulation of T cell activation, and ultimately seems to exert this effect by regulating T cell cytokine gene expression via tyrosine phosphorylation of certain intracellular substrates such as certain phospholipases. (see Linsley et al., Ann. Rev. Immunol., 11:191–212 [1993]).

Another protein that is important in immune system regulation is the cell surface receptor molecule known as CD45 receptor or CD45. This molecule is expressed on the surface of many types of hematopoietic cells, including for example B cells and certain T cells. The gene encoding CD45 undergoes alternative splicing. CD45 has 34 exons (Johnson et al., J. Biol. Chem., 264:6220–6229 [1989]). As a result, there are multiple isoforms of CD45 (Trowbridge et al., Biochem, Biophys. Acta, 1095: 46–56 [1991], primarily due to alternative splicing of exons 4, 5, and 6. Different isoforms are expressed on different cells, but one cell type may express more than one isoform (Thomas, Ann. Rev. Immunol., 7:339–369 [1989]; Trowbridge et al., supra). CD45 has a molecular weight of between about 180kD and 235 kD, depending on the isoform. The approximately 180kD isoform, known as CD45RO, does not express exons 4, 5, or 6. CD45 is a protein tyrosine phosphatase and is involved in cell signaling (Charbonneau et al., Proc. Natl. Acad. Sci USA 85:7182–7186 [1988]; Tonks et al., Biochem., 27:8695–8701 [1988]). It has been suggested that CD45 may form a complex with proteins that are associated with antigen receptors expressed on the cell surface, and may regulate signal transduction by modulating the phosphorylation of these receptors (Justement et al., Science, 252: 1839–1842 [1991]).

Murine T cell clones lacking expression of CD45 have been generated by chemical mutagenesis (Pingel et al., Cell, 58:1055–1065 [1989]; Weaver et al., Mol. Cell. Biol., 11:4415–4422 [1991]). These cells failed to become activated (i.e., to proliferate) in response to certain compounds that normally serve as activation signals. The cells had other impaired functions as well such as decreased cytokine production.

A mutant human T cell leukemia cell line with suppressed CD45 expression has been generated using gamma irradiation (Koretzky et al., Proc. Natl.Acad. Sci. USA, 88:2037–2041 [1991]; Koretzky et al., Nature, 346: 66–68 [1990]). Among other impaired functions, this cell line was shown to lack the ability to activate a T cell receptor associated tyrosine kinase.

While the use of isolated cell lines is helpful in understanding the role of various proteins on immune system regulation, more complete information can be obtained by studying the effects of these proteins directly in a mammal (i.e., an in vivo system). To this end, various mammals have been produced that have altered levels of expression of certain genes. One class of these mammals are the so called transgenic mammals. These mammals have a novel gene or genes introduced into their genome. Another class of these mammals is the so called knockout mammals, wherein expression of an endogenous gene has been suppressed through genetic manipulation.

A variety of transgenic mammals have been developed. For example, U.S. Pat. No. 4,736,866 issued Apr. 12, 1988 describes a mouse containing a transgene encoding an oncogene.

U.S. Pat. No. 5,175,384, issued Dec. 29, 1992, describes a transgenic mouse deficient in mature T cells.

U.S. Pat. No. 5,175,383, issued Dec. 29, 1992, describes a mouse with a transgene encoding a gene in the int-2/ FGF family. This gene promotes benign prostatic hyperplasia.

U.S. Pat. No. 5,175,385, issued Dec. 29, 1992, describes a transgenic mouse with enhanced resistance to certain viruses.

PCT patent application no. WO 92/22645, published Dec. 23, 1992, describes a transgenic mouse deficient in certain lymphoid cell types.

Preparation of a knockout mammal requires first introducing a nucleic acid construct that will be used to suppress expression of a particular gene into an undifferentiated cell type termed an embryonic stem cell. This cell is then injected into a mammalian embryo, where it hopefully will be integrated into the developing embryo. The embryo is then implanted into a foster mother for the duration of gestation.

Pfeffer et al. (*Cell*, 73:457–467 [1993]) describe mice in which the gene encoding the tumor necrosis factor receptor p55 has been suppressed. The mice showed a decreased response to tumor necrosis factor signaling.

Fung-Leung et al. (*Cell*, 65:443–449 [1991]; *J. Exp. Med.*, 174:1425–1429 [1991]) describe knockout mice lacking expression of the gene encoding CD8. These mice were found to have a decreased level of cytotoxic T cell response to various antigens and to certain viral pathogens such as lymphocytic choriomeningitis virus.

Kishihara et al. (*Cell*, 74:143–156 [1993]) describe generation of a mouse with a mutation in exon 6 of CD45. This mouse reportedly does not express CD45 in most B and T cells.

In view of the devastating effects that can result from immune disorders, there is a need in the art to provide in vivo systems for screening and evaluating drugs useful in the treatment of these disorders.

Accordingly, it is an object of this invention to provide mammals in which a gene involved in regulation of the immune system has been suppressed through the use of knockout technology, and/or a novel gene is expressed in the mammal such that the mammal may be a knockout transgenic mammal.

It is a further object of this invention to provide methods for preparing, and to prepare such knockout and knockout transgenic mammals.

These and other such objects will readily be apparent to one of ordinary skill in the art.

SUMMARY OF THE INVENTION

In one aspect, the invention provides a mouse and its progeny having a suppressed level of expression of the gene encoding CD28 on T cells. The gene may be suppressed by insertion into the genome of the mouse a nucleic acid sequence comprising at least a portion of an exon of the CD28 coding sequence linked to a marker sequence; the marker sequence can be the neomycin resistance gene.

In another aspect, the invention provides a mouse and its progeny wherein expression of the gene encoding CD45 is suppressed on B cells. The invention further provides mice with a decreased level of CD45 expression on thymocytes and peripheral T cells. Expression of the CD45 gene may be suppressed or decreased by insertion into the genome of the mouse a nucleic acid sequence comprising at least a portion of one exon of CD45 linked to a marker sequence such as the neomycin resistance gene sequence.

In a preferred embodiment, the CD45 gene that is suppressed or decreased is the CD45 exon 6 isoform.

In yet another aspect, the invention provides a mouse and its progeny wherein expression of the endogenous gene encoding CD45 isoform 6 has been suppressed, and wherein the mouse is capable of expressing a novel nucleotide sequence or transgene.

In other aspects, the invention provides embryonic stem cell lines containing a CD28 or a CD45 exon 6 isoform knockout construct.

In yet one other aspect, the invention provides a method of screening a drug for immunostimulatory effects comprising administering the drug to a mouse with a suppressed level of CD28 or CD45 expression, and assaying the mouse for immunostimulation.

BRIEF DESCRIPTION OF THE DRAWINGS

FIG. 5 depicts the proliferation of splenocytes from wild type (solid bars), heterozygous CD45 knockout (single hatched bars) or homozygous CD45 knockout (double hatched bars) mice in response to either 1) lipopolysaccharide (LPS), or 2) purified anti-$\mu$ antibodies (B-7-6). These data were obtained 3, 4, or 5 days after the stimulants were added to the culture media. "N.S." indicates no stimulant added.

DETAILED DESCRIPTION OF THE INVENTION

Figure 1A:
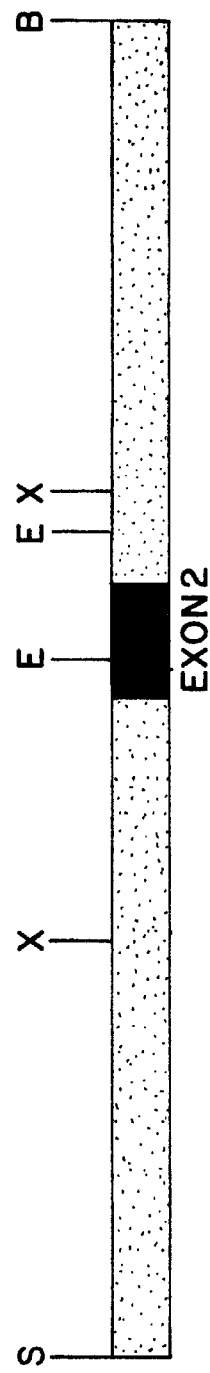
FIGS. 1(A–C) depicts the knockout construct used to suppress expression of CD28. 1A depicts the structure of a portion of the native CD28 gene. 1B depicts the CD28 knockout construct generated, and 1C depicts this knockout construct inserted into the native CD28 gene after homologous recombination. Restriction enzymes used are indicated by one letter abbreviations. S=SalI; X=XbaI; E=EcoRI; and B=BamHI.
Figure 1B:
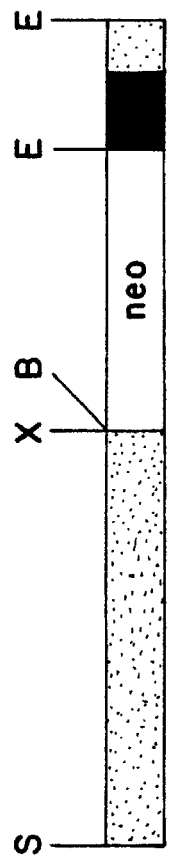
Figure 1C:
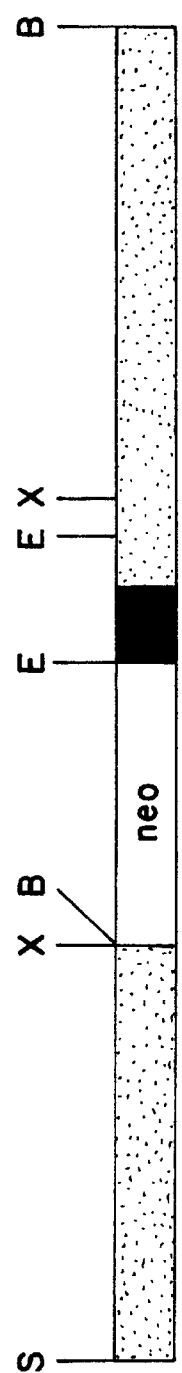

This invention is based in part on the discovery that the level of expression of a particular gene in a mammal can be decreased or even completely suppressed by introducing into the genomic DNA of the mammal a new DNA sequence that serves to interrupt some portion of the DNA sequence of the gene to be suppressed.

The term "knockout" refers to partial or complete suppression of the expression of at least a portion of a protein encoded by an endogenous DNA sequence in a cell.

The term "knockout construct" refers to a nucleic acid sequence that is designed to decrease or suppress expression of a protein encoded by endogenous DNA sequences in a cell. The nucleic acid sequence used as the knockout construct is typically comprised of (1) DNA from some portion of the gene (exon sequence, intron sequence, and/or promoter sequence) to be suppressed and (2) a marker sequence used to detect the presence of the knockout construct in the cell. The knockout construct is inserted into a cell, and integrates with the genomic DNA of the cell in such a position so as to prevent or interrupt transcription of the native DNA sequence. Such insertion usually occurs by homologous recombination (i.e., regions of the knockout construct that are homologous to endogenous DNA sequences hybridize to each other when the knockout construct is inserted into the cell and recombine so that the knockout construct is incorporated into the corresponding position of the endogenous DNA). The knockout construct nucleic acid sequence may comprise 1) a full or partial sequence of one or more exons and/or introns of the gene to be suppressed, 2) a full or partial promoter sequence of the gene to be suppressed, or 3) combinations thereof.

Typically, the knockout construct is inserted into an embryonic stem cell (ES cell) and is integrated into the ES cell genomic DNA, usually by the process of homologous recombination. This ES cell is then injected into, and integrates with, the developing embryo.

The phrases "disruption of the gene" and "gene disruption" refer to insertion of a nucleic acid sequence into one region of the native DNA sequence (usually one or more exons) and/or the promoter region of a gene so as to decrease or prevent expression of that gene in the cell as compared to the wild-type or naturally occurring sequence of the gene. By way of example, a nucleic acid construct can be prepared containing a DNA sequence encoding an antibiotic resistance gene which is inserted into the DNA sequence that is complementary to the DNA sequence (promoter and/or coding region) to be disrupted. When this nucleic acid construct is then transfected into a cell, the construct will integrate into the genomic DNA. Thus, many progeny of the cell will no longer express the gene at least in some cells, or will express it at a decreased level, as the DNA is now disrupted by the antibiotic resistance gene.

The term "transgene" refers to an isolated nucleotide sequence that may be inserted into one or more cells of a mammal or mammalian embryo. The transgene optionally may be operably linked to other genetic elements (such as a promoter, poly A sequence and the like) that may serve to modulate, either directly, or indirectly in conjunction with the cellular machinery, the transcription and/or expression of the transgene. Alternatively or additionally, the transgene may be linked to nucleotide sequences that aid in integration of the transgene into the chromosomal DNA of the mammalian cell or embryo nucleus (as for example, in homologous recombination). The transgene may be comprised of a nucleotide sequence that is either homologous or heterologous to a particular nucleotide sequence in the mammal's endogenous genetic material, or is a hybrid sequence (i.e. one or more portions of the transgene are homologous, and one or more portions are heterologous to the mammal's genetic material). The transgene nucleotide sequence may encode a polypeptide or a variant of a polypeptide, found endogenously in the mammal, it may encode a polypeptide not naturally occurring in the mammal (i.e. an exogenous polypeptide), or it may encode a hybrid of endogenous and exogenous polypeptides. Where the transgene is operably linked to a promoter, the promoter may be homologous or heterologous to the mammal and/or to the transgene. Alternatively, the promoter may be a hybrid of endogenous and exogenous promoter elements (enhancers, silencers, suppressors, and the like).

The terms "CD28" and "CD28 receptor" refer to a cell surface receptor protein that is expressed on certain cells of the immune system, especially T cells. The engagement of CD28 with its ligands B7/BB1, is believed to be an essential co-stimulatory signal necessary for activation of T cells.

The term "CD45", "CD45 receptor" and "L-CA" refer to a cell surface receptor glycoprotein expressed on the surface of many types of hematopoietic cells. CD45 has multiple isoforms ranging in molecular weight from about 180kD to about 235 kD. Different hematopoietic cell lines express different isoforms of CD45, and some cells may express more than one isoform. As used herein CD45 refers to any and all of these isoforms.

The term "CD45 exon 6 isoform" refers to the CD45 isoform that expresses exon 6 (as well as other exons) of the CD45 gene. "CD45 exon 6 isoform knockout construct" refers to a knockout construct designed to suppress expression of the CD45 isoform expressing exon 6 (as well as other exons).

The term "CD45RO" refers to the CD45 isoform in which exons 4, 5, and 6 of the CD45 gene are not expressed.

The term "marker sequence" refers to a nucleic acid sequence that is (1) used as part of a nucleic acid construct (i.e., the "knockout construct") to disrupt the expression of the gene(s) of interest (such as, for example, CD28 or CD45), and (2) used as a means to identify those cells that have incorporated the knockout construct into the genome. The marker sequence may be any sequence that serves these purposes, although typically it will be a sequence encoding a protein that confers a detectable trait on the cell, such as an antibiotic resistance gene or an assayable enzyme not typically found in the cell. Where the marker sequence encodes a protein, the marker sequence will also typically contain a promoter that regulates its expression.

The terms "rodent" and "rodents" refer to all members of the phylogenetic order Rodentia including any and all progeny of all future generations derived therefrom.

The term "murine" refers to any and all members of the family Muridae, including rats and mice.

The term "progeny" refers to any and all future generations derived and descending from a particular mammal, i.e., a mammal containing a knockout construct inserted into its genomic DNA. Thus, progeny of any successive generation are included herein such that the progeny, the F1, F2, F3, generations and so on indefinitely are included in this definition.

The terms "immunomodulate" and "immunomodulation" refer to changes in the level of activity of any components of the immune system as compared to the average activity of that component for a particular species. Thus, as used herein, immunomodulation refers to an increase or a decrease in activity. Immunomodulation may be detected by assaying the level of B cells, any or all types of T cells, antigen presenting cells, and any other cells believed to be involved in immune function. Additionally or alternatively, immunomodulation may be detected by evaluating 1) the level of expression of particular genes believed to have a role in the immune system, 2) the level of particular compounds such as cytokines (interleukins and the like) or other molecules that have a role in the immune system, and/or 3) the level of particular enzymes, proteins, and the like that are involved in immune system functioning.

The term "operably linked" refers to the arrangement of various nucleotide sequences relative to each other such that the elements are functionally connected and are able to interact with each other. Such elements may include, without limitation, one or more promoters, enhancers, polyadenylation sequences, and transgenes. The nucleotide sequence elements, when properly oriented, or operably linked, act together to modulate the activity of one another, and ultimately may affect the level of expression of the transgene(s). By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements.

The term "biologically active fragment" refers to a nucleotide sequence that is less than the full-length genomic or cDNA nucleotide sequence of a gene or transgene, but contains a sufficient portion of the full length nucleotide sequence such that the gene (or transgene) product of the biologically active fragment possesses at least a portion of the biological activity possessed by the gene product of the full length sequence.

Knockout Technology
1. Selection of Knockout Gene(s)

The gene to be knocked out may be any gene provided that at least some sequence information on the DNA to be disrupted is available to use in the preparation of both the knockout construct and the screening probes. Usually, the DNA to be used in the knockout construct will be one or more exon and/or intron regions, and/or a promoter region, but may also be a cDNA sequence provided the cDNA is sufficiently large. Generally, the DNA will be at least about 1 kilobase (kb) in length and preferably 3–4 kb in length, thereby providing sufficient complementary sequence for hybridization when the knockout construct is introduced into the genomic DNA of the ES cell (discussed below). Typically, the gene to be knocked out will be a gene that 1) is expressed in mature and/or immature T cells and/or B cells, 2) is involved, either directly or indirectly, in the activation pathway during inflammation or immunosuppression responses by the immune system, and 3) does not result in lethality when knocked out. Preferred genes to be knocked out are the CD28 and CD45 genes.

Included within the scope of this invention is a mammal in which two or more genes have been knocked out. Such mammals can be generated by repeating the procedures set forth herein for generating each knockout construct, or by breeding to mammals, each with a single gene knocked out, to each other, and screening for those with the double knockout genotype.

The DNA sequence to be used to knock out a selected gene can be obtained using methods well known in the art such as those described by Sambrook et al. (*Molecular Cloning: A Laboratory Manual*, Cold Spring Harbor Laboratory Press, Cold Spring Harbor, N.Y. [1989]). Such methods include, for example, screening a genomic library with a cDNA probe encoding at least a portion of the same gene in order to obtain at least a portion of the genomic sequence. Alternatively, if a cDNA sequence is to be used in a knockout construct, the cDNA may be obtained by screening a cDNA library with oligonucleotide probes or antibodies (where the library is cloned into an expression vector). If a promoter sequence is to-be used in the knockout construct, synthetic DNA probes can be designed for screening a genomic library containing the promoter sequence.

Another method for obtaining the DNA to be used in the knockout construct is to manufacture the DNA sequence synthetically, using a DNA synthesizer.

The DNA sequence encoding the knockout construct must be generated in sufficient quantity for genetic manipulation and insertion into ES cells. Amplification may be conducted by 1) placing the sequence into a suitable vector and transforming bacterial or other cells that can rapidly amplify the vector, 2) by PCR amplification, or 3) by synthesis with a DNA synthesizer.

2. Preparation of Knockout Constructs

The DNA sequence to be used in producing the knockout construct is digested with a particular restriction enzyme selected to cut at a location(s) such that a new DNA sequence encoding a marker gene can be inserted in the proper position within this DNA sequence. The proper position for marker gene insertion is that which will serve to prevent expression of the native gene; this position will depend on various factors such as the restriction sites in the sequence to be cut, and whether an exon sequence or a promoter sequence, or both is (are) to be interrupted (i.e., the precise location of insertion necessary to inhibit promoter function or to inhibit synthesis of the native exon). Preferably, the enzyme selected for cutting the DNA will generate a longer arm and a shorter arm, where the shorter arm is at least about 300 base pairs (bp). In some cases, it will be desirable to actually remove a portion or even all of one or more exons of the gene to be suppressed so as to keep the length of the knockout construct comparable to the original genomic sequence when the marker gene is inserted in the knockout construct. In these cases, the genomic DNA is cut with appropriate restriction endonucleases such that a fragment of the proper size can be removed.

The marker gene can be any nucleic acid sequence that is detectable and/or assayable, however typically it is an antibiotic resistance gene or other gene whose expression or presence in the genome can easily be detected. The marker gene is usually operably linked to its own promoter or to another strong promoter from any source that will be active or can easily be activated in the cell into which it is inserted; however, the marker gene need not have its own promoter attached as it may be transcribed using the promoter of the gene to be suppressed. In addition, the marker gene will normally have a polyA sequence attached to the 3' end of the gene; this sequence serves to terminate transcription of the gene. Preferred marker genes are any antibiotic resistance gene such as neo (the neomycin resistance gene) and beta-gal (beta-galactosidase).

After the genomic DNA sequence has been digested with the appropriate restriction enzymes, the marker gene sequence is ligated into the genomic DNA sequence using methods well known to the skilled artisan and described in Sambrook et al., supra. The ends of the DNA fragments to be ligated must be compatible; this is achieved by either cutting all fragments with enzymes that generate compatible ends, or by blunting the ends prior to ligation. Blunting is done using methods well known in the art, such as for example by the use of Klenow fragment (DNA polymerase I) to fill in sticky ends.

The ligated knockout construct may be inserted directly into embryonic stem cells (discussed below), or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

3. Transfection of Embryonic Stem Cells

This invention contemplates production of knockout mammals from any species of rodent, including without limitation, rabbits, rats, hamsters, and mice. Preferred rodents include members of the Muridae family, including rats and mice. Generally, the embryonic stem cells (ES cells) used to produce the knockout mammal will be of the same species as the knockout mammal to be generated. Thus for example, mouse embryonic stem cells will usually be used for generation of knockout mice.

Embryonic stem cells are typically selected for their ability to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. A preferred ES cell line is murine cell line D3 (American Type Culture Collection catalog no. CRL 1934). The cells are cultured and prepared for DNA insertion using methods well known to the skilled artisan such as those set forth by Robertson (in:*Teratocarcinomas and Embryonic Stem Cells: A Practical Approach*, E. J. Robertson, ed. IRL Press, Washington, D.C. [1987]) and by Bradley et al. (*Current Topics in Devel. Biol.*, 20:357–371 [1986]) and by Hogan et al. (*Manipulating the Mouse Embryo: A Laboratory Manual*, Cold Spring Harbor Laboratory Press, Cold Spring Harbor, N.Y. [1986]).

Insertion of the knockout construct into the ES cells can be accomplished using a variety of methods well known in the art including for example, electroporation, microinjection, and calcium phosphate treatment (see Lovell-Badge, in Robertson, ed., supra). A preferred method of insertion is electroporation.

Each knockout construct DNA to be inserted into the cell must first be linearized if the knockout construct has been inserted into a vector. Linearization is accomplished by digesting the DNA with a suitable restriction endonuclease selected to cut only within the vector sequence and not within the knockout construct sequence.

For insertion of the DNA sequence, the knockout construct DNA is added to the ES cells under appropriate conditions for the insertion method chosen. Where more than one construct is to be introduced into the ES cell, DNA encoding each construct can be introduced simultaneously or one at a time.

If the cells are to be electroporated, the ES cells and knockout construct DNA are exposed to an electric pulse using an electroporation machine and following the manufacturer's guidelines for use. After electroporation, the cells are allowed to recover under suitable incubation conditions. The cells are then screened for the presence of the knockout construct.

Screening can be done using a variety of methods. Where the marker gene is an antibiotic resistance gene, the cells are cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. Finally, if the marker gene is a gene that encodes an enzyme whose activity can be detected (e.g., beta-galactosidase), the enzyme substrate can be added to the cells under suitable conditions, and the enzymatic activity can be analyzed.

The knockout construct may be integrated into several locations in the ES cell genome, and may integrate into a different location in each cell's genome, due to the occurrence of random insertion events; the desired location of the insertion is in a complementary position to the DNA sequence to be knocked out. Typically, less than about 1–5 percent of the ES cells that take up the knockout construct will actually integrate the knockout construct in the desired location. To identify those cells with proper integration of the knockout construct, the DNA can be extracted from the cells using standard methods such as those described by Sambrook et al., supra. The DNA can then be probed on a Southern blot with a probe or probes designed to hybridize in a specific pattern to genomic DNA digested with (a) particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

4. Injection/Implantation of Embryos

After suitable ES cells containing the knockout construct in the proper location have been identified, the cells are inserted into an embryo. Insertion may be accomplished in a variety of ways, however a preferred method is by microinjection. For microinjection, about 10–30 cells are collected into a micropipet and injected into embryos that are at the proper stage of development to integrate the ES cell into the developing embryo.

The suitable stage of development for the embryo is very species dependent, however for mice it is about 3.5 days. The embryos are obtained by perfusing the uterus of pregnant females. Suitable methods for accomplishing this are known to the skilled artisan, and are set forth by Bradley (in Robertson, ed., supra).

While any embryo of the right age/stage of development is suitable for use, preferred embryos are male and have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo is implanted into the uterus of a pseudopregnant foster mother. While any foster mother may be used, they are typically selected for their ability to breed and reproduce well, and for their ability to care for their young. Such foster mothers are typically prepared by mating with vasectomized males of the same species. The stage of the pseudopregnant foster mother is important for successful implantation, and it is species dependent. For mice, this stage is about 2–3 days pseudopregnant.

5. Screening for Presence of Knockout Gene

Offspring that are born to the foster mother may be screened initially for mosaic coat color where the coat color selection strategy (as described above) has been employed. In addition, or as an alternative, DNA from tail tissue of the offspring may be screened for the presence of the knockout construct using Southern blots and/or PCR as described above. Offspring that appear to be mosaics are then crossed to each other if they are believed to carry the knockout construct in their germ line to generate homozygous knockout animals. If it is unclear whether the offspring will have germ line transmission, they can be crossed with a parental or other strain and the offspring screened for heterozygosity. The heterozygotes are identified by Southern blots and/or PCR amplification of the DNA, as set forth above.

The heterozygotes can then be crossed with each other to generate homozygous knockout offspring. Homozygotes may be identified by Southern blotting of equivalent amounts of genomic DNA from mice that are the product of this cross, as well as mice that are known heterozygotes and wild type mice. Probes to screen the Southern blots can be designed as set forth above.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the gene knocked out in various tissues of these offspring by probing the Western blot with an antibody against the protein encoded by the gene knocked out, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Transgene Technology

1. Selection of Transgene(s)

Typically, the transgene(s) useful in the present invention will be a nucleotide sequence encoding a polypeptide involved in the immune response, hematopoiesis, inflammation, cell growth and proliferation, cell lineage differentiation, and/or the stress response. Preferred transgenes are those that comprise polypeptides of the immune system, such as various isoforms of CD45, especially CD45RO.

Included within the scope of this invention is the insertion of two or more transgenes into a mammal.

Where more than one transgene is used in this invention, the transgenes may be prepared and inserted individually, or may be generated together as one construct for insertion. The transgenes may be homologous or heterologous to both the promoter selected to drive expression of each transgene and/or to the mammal. Further, the transgene may be a full length cDNA or genomic DNA sequence, or any fragment, subunit or mutant thereof that has at least some biological activity i.e., exhibits an effect at any level (biochemical, cellular and/or morphological) that is not readily observed in a wild type, non-transgenic mammal of the same species. Optionally, the transgene may be a hybrid nucleotide sequence, i.e., one constructed from homologous and/or heterologous cDNA and/or genomic DNA fragments. The transgene may also optionally be a mutant of one or more naturally occurring cDNA and/or genomic sequences, or an allelic variant thereof.

Each transgene may be isolated and obtained in suitable quantity using one or more methods that are well known in the art. These methods and others useful for isolating a transgene are set forth, for example, in Sambrook et al. (*Molecular Cloning: A Laboratory Manual*, Cold Spring Harbor Laboratory Press, Cold Spring Harbor, N.Y. [1989]) and in Berger and Kimmel (*Methods in Enzymology: Guide to Molecular Cloning Techniques*, vol. 152, Academic Press, Inc., San Diego, Calif. [1987]).

Where the nucleotide sequence of each transgene is known, the transgene may be synthesized, in whole or in part, using chemical synthesis methods such as those described in Engels et al. (*Angew. Chem. Int. Ed. Engl.*, 28:716–734 [1989]). These methods include, inter alia, the phosphotriester, phosphoramidite and H-phosphonate methods of nucleic acid synthesis. Alternatively, the transgene may be obtained by screening an appropriate cDNA or genomic library using one or more nucleic acid probes (oligonucleotides, cDNA or genomic DNA fragments with an acceptable level of homology to the transgene to be cloned, and the like) that will hybridize selectively with the transgene DNA. Another suitable method for obtaining a transgene is the polymerase chain reaction (PCR). However, successful use of this method requires that enough information about the nucleotide sequence of the transgene be available so as to design suitable oligonucleotide primers useful for amplification of the appropriate nucleotide sequence.

Where the method of choice requires the use of oligonucleotide primers or probes (e.g. PCR, cDNA or genomic library screening), the oligonucleotide sequences selected as probes or primers should be of adequate length and sufficiently unambiguous so as to minimize the amount of non-specific binding that will occur during library screening or PCR. The actual sequence of the probes or primers is usually based on conserved or highly homologous sequences or regions from the same or a similar gene from another organism. Optionally, the probes or primers can be degenerate.

In cases where only the amino acid sequence of the transgene is known, a probable and functional nucleic acid sequence may be inferred for the transgene using known and preferred codons for each amino acid residue. This sequence can then be chemically synthesized.

This invention contemplates the use of transgene mutant sequences. A mutant transgene is a transgene containing one or more nucleotide substitutions, deletions, and/or insertions as compared to the wild type sequence. The nucleotide substitution, deletion, and/or insertion can give rise to a gene product (i.e., protein) that is different in its amino acid sequence from the wild type amino acid sequence. Preparation of such mutants is well known in the art, and is described for example in Wells et al. (Gene, 34:315 [1985]), and in Sambrook et al, supra.

2. Selection of Reaulatory Elements

The transgenes of the present invention are typically operably linked to promoters, where a promoter is selected to regulate expression of each transgene in a particular manner.

Where more than one transgene is to be used, each transgene may be regulated by the same or by a different promoter. The selected promoters may be homologous (i.e., from the same species as the mammal to be transfected with the transgene) or heterologous (i.e., from a source other than the species of the mammal to be transfected with the transgene). As such, the source of each promoter may be from any unicellular, prokaryotic or eukaryotic organism, or any vertebrate or invertebrate organism. The more preferred promoters of this invention are promoters that regulate expression of genes of the immune system such as the CD45 promoter, the mouse lck promoter, and the mouse H-2kb promoter operably linked to the human beta-globin 3' region and to the mouse Igu enhancer. The most preferred promoter is the mouse lck promoter.

The promoters of this invention may be used alone or in combination with homologous and/or heterologous enhancers and/or silencers in order to permit a tighter regulation of expression.

The nucleotide sequences of the promoters of this invention may be obtained by any of several methods well known in the art. Typically, promoters useful herein will have been previously identified by mapping and/or by restriction endonuclease digestion and can thus be isolated from the genomic DNA of the proper tissue source using the appropriate restriction endonucleases. In some cases, the promoter may have been sequenced. For those promoters whose nucleotide sequence is known, the promoter may be synthesized using the methods described above for transgene synthesis.

Where all or only portions of the promoter sequence are known, the promoter may be obtained using PCR and/or by screening a genomic library with suitable oligonucleotide and/or promoter sequence fragments from the same or another species.

Where the promoter sequence is not known, a fragment of DNA containing the promoter may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment is isolated by agarose gel purification, Qiagen® column (Qiagen Corp., Chatsworth, Calif.) or other methods known to the skilled artisan. Selection of suitable enzymes to accomplish this purpose will be readily apparent to one of ordinary skill in the art.

3. Selection of Other Vector Components

In addition to the transgene and the promoter, the vectors useful for preparing the transgenes of this invention typically contain one or more other elements useful for (1) optimal expression of transgene in the mammal into which the transgene is inserted, and (2) amplification of the vector in bacterial or mammalian host cells. Each of these elements will be positioned appropriately in the vector with respect to each other element so as to maximize their respective activities. Such positioning is well known to the ordinary skilled artisan. The following elements may be optionally included in the vector as appropriate.

i. Signal Sequence Element

For those embodiments of the invention where the polypeptide encoded by the transgene is to be secreted, a small polypeptide termed signal sequence is frequently present to direct the polypeptide encoded by the transgene out of the cell where it is synthesized. Typically, the signal sequence is positioned in the coding region of the transgene towards or at the 5' end of the coding region. Many signal sequences have been identified, and any of them that are functional and thus compatible with the transgenic tissue may be used in conjunction with the transgene. Therefore, the nucleotide sequence encoding the signal sequence may be homologous or heterologous to the transgene, and may be homologous or heterologous to the transgenic mammal. Additionally, the nucleotide sequence encoding the signal sequence may be chemically synthesized using methods set forth above. However, for purposes herein, preferred signal sequences are those that occur naturally with the transgene (i.e., are homologous to the transgene).

ii. Membrane Anchoring Domain Element

In some cases, it may be desirable to have a transgene expressed on the surface of a particular intracellular membrane or on the plasma membrane. Naturally occurring membrane proteins contain, as part of the polypeptide, a stretch of amino acids that serve to anchor the protein to the membrane. However, for proteins that are not naturally found on the membrane, such a stretch of amino acids may be added to confer this feature. Frequently, the anchor domain will be an internal portion of the polypeptide sequence and thus the nucleotide sequence encoding it will be engineered into an internal region of the transgene nucleotide sequence. However, in other cases, the nucleotide sequence encoding the anchor domain may be attached to the 5' or 3' end of the transgene nucleotide sequence. Here, the nucleotide sequence encoding the anchor domain may first be placed into the vector in the appropriate position as a separate component from the nucleotide sequence encoding the transgene. As for the signal sequence, the anchor domain may be from any source and thus may be homologous or heterologous with respect to both the transgene and the transgenic mammal. Alternatively, the anchor domain may be chemically synthesized using methods set forth above.

iii. Origin of Replication Element

This component is typically a part of prokaryotic expression vectors purchased commercially, and aids in the amplification of the vector in a host cell. If the vector of choice does not contain an origin of replication site, one may be chemically synthesized based on a known sequence, and ligated into the vector.

iv. Transcription Termination Element

This element, also known as the polyadenylation or polyA sequence, is typically located 3' to the transgene nucleotide sequence in the vector, and serves to terminate transcription of the transgene. While the nucleotide sequence encoding this element is easily cloned from a library or even purchased commercially as part of a vector, it can also be readily synthesized using methods for nucleotide sequence synthesis such as those described above.

v. Intron Element

In many cases, transcription of the transgene is increased by the presence of one intron or more than one intron (linked by exons) on the cloning vector. The intron(s) may be naturally occurring within the transgene nucleotide sequence, especially where the transgene is a full length or a fragment of a genomic DNA sequence. Where the intron(s) is not naturally occurring within the nucleotide sequence (as for most cDNAs), the intron(s) may be obtained from another source. The intron(s) may be homologous or heterologous to the transgene and/or to the transgenic mammal. The position of the intron with respect to the promoter and the transgene is important, as the intron must be transcribed to be effective. As such, where the transgene is a cDNA sequence, the preferred position for the intron(s) is 3' to the transcription start site, and 5' to the polyA transcription termination sequence. Preferably for cDNA transgenes, the intron will be located on one side or the other (i.e., 5' or 3') of the transgene nucleotide sequence such that it does not interrupt the transgene nucleotide sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector. A preferred set of introns and exons is the human growth hormone (hGH) DNA sequence.

vi. Selectable Marker(s) Element

Selectable marker genes encode polypeptides necessary for the survival and growth of transfected cells grown in a selective culture medium. Typical selection marker genes encode proteins that (a) confer resistance to antibiotics or other toxins, e.g., ampicillin, tetracycline, or kanomycin for prokaryotic host cells, and neomycin, hygromycin, or methotrexate for mammalian cells; (b) complement auxotrophic deficiencies of the cell; or (c) supply critical nutrients not available from complex media, e.g., the gene encoding D-alanine racemase for cultures of Bacilli.

All of the elements set forth above, as well as others useful in this invention, are well known to the skilled artisan and are described, for example, in Sambrook et al. (*Molecular Cloning: A Laboratory Manual*, Cold Spring Harbor Laboratory Press, Cold Spring Harbor, N.Y. [1989]) and Berger et al., eds. (*Guide to Molecular Cloning Techniques*, Academic Press, Inc., San Diego, Calif. [1987]).

4. Construction of Cloning Vectors

The cloning vectors most useful for amplification of transgene cassettes useful in preparing the transgenic mammals of this invention are those that are compatible with prokaryotic cell hosts. However, eukaryotic cell hosts, and vectors compatible with these cells, are within the scope of the invention.

In certain cases, some of the various elements to be contained on the cloning vector may be already present in commercially available cloning or amplification vectors such as pUC18, pUC19, pBR322, the pGEM vectors (Promega Corp, Madison, Wis.), the pBluescript® vectors such as pBIISK+/− (Stratagene Corp., La Jolla, Calif.), and the like, all of which are suitable for prokaryotic cell hosts. In this case it is necessary to only insert the transgene(s) into the vector.

However, where one or more of the elements to be used are not already present on the cloning or amplification vector, they may be individually obtained and ligated into the vector. Methods used for obtaining each of the elements and ligating them are well known to the skilled artisan and are comparable to the methods set forth above for obtaining a transgene (i.e., synthesis of the DNA, library screening, and the like).

Vectors used for cloning or amplification of the transgene (s) nucleotide sequences and/or for transfection of the mammalian embryos are constructed using methods well known in the art. Such methods include, for example, the standard techniques of restriction endonuclease digestion, ligation, agarose and acrylamide gel purification of DNA and/or RNA, column chromatography purification of DNA and/or RNA, phenol/chloroform extraction of DNA, DNA sequencing, polymerase chain reaction amplification, and the like, as set forth in Sambrook et al., supra.

The final vector used to practice this invention is typically constructed from a starting cloning or amplification vector such as a commercially available vector. This vector may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector is to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

After the vector has been constructed, it may be transfected into a prokaryotic host cell for amplification. Cells typically used for amplification are *E coli* DH5-alpha (Gibco/BRL, Grand Island, N.Y.) and other *E. coli* strains with characteristics similar to DH5-alpha.

Where mammalian host cells are used, cell lines such as Chinese hamster ovary (CHO cells; Urlab et al., *Proc. Natl. Acad. Sci USA*, 77:4216 [1980])) and human embryonic kidney cell line 293 (Graham et al., *J. Gen. Virol.*, 36:59 [1977]), as well as other lines, are suitable.

Transfection of the vector into the selected host cell line for amplification is accomplished using such methods as calcium phosphate, electroporation, microinjection, lipofection or DEAE-dextran. The method selected will in part be a function of the type of host cell to be transfected. These methods and other suitable methods are well known to the skilled artisan, and are set forth in Sambrook et al., supra.

After culturing the cells long enough for the vector to be sufficiently amplified (usually overnight for *E. coli* cells), the vector (often termed plasmid at this stage) is isolated from the cells and purified. Typically, the cells are lysed and the plasmid is extracted from other cell contents. Methods suitable for plasmid purification include inter alla, the alkaline lysis mini-prep method (Sambrook et al., supra).

5. Preparation of Plasmid For Insertion

Typically, the plasmid containing the transgene is linearized, and portions of it removed using a selected restriction endonuclease prior to insertion into the embryo. In some cases, it may be preferable to isolate the transgene, promoter, and regulatory elements as a linear fragment from the other portions of the vector, thereby injecting only a linear nucleotide sequence containing the transgene, promoter, intron (if one is to be used), enhancer, polyA sequence, and optionally a signal sequence or membrane anchoring domain into the embryo. This may be accomplished by cutting the plasmid so as to remove the nucleic acid sequence region containing these elements, and purifying this region using agarose gel electrophoresis or other suitable purification methods.

6. Production of Transgenic Mammals

Transgenic mammals may readily be prepared using methods well known to the skilled artisan. Foe example, to prepare transgenic rodents, methods such as those set forth by Hogan et al., eds., (*Manipulating the Mouse Embryo: A Laboratory Manual*, Cold Spring Harbor Laboratory Press, Cold Spring Harbor, N.Y. [1986]) may be employed.

The specific line(s) of any mammalian species used to practice this invention are selected for general good health, good embryo yields, good pronuclear visibility in the embryos, and good reproductive fitness. In addition, the haplotype is a significant factor. For example, when transgenic mice are to be produced, strains such as C57BL/6 or C57BL/6 ×DBA/2 $F_1$, or FVB lines are often used (obtained commercially from Charles River Labs, Boston, Mass., The Jackson Laboratory, Bar Harbor, ME, or Taconic Labs.). Preferred strains are those with $H-2^b$, $H-2^d$ or $H-2^q$ haplotypes such as C57BL/6 or DBA/1. The line(s) used to practice this invention may themselves be transgenics, and/ or may be knockouts (i.e., mammals which have one or more genes partially or completely suppressed). Preferably the same line will be used for preparation of both the initial knockout mammals and the transgenic mammals. This will make subsequent breeding and backcrossing more efficient.

The age of the mammals that are used to obtain embryos and to serve as surrogate hosts is a function of the species used, but is readily determined by one of ordinary skill in the art. For example, when mice are used, pre-puberal females are preferred, as they yield more embryos and respond better to hormone injections.

Similarly, the male mammal to be used as a stud will normally be selected by age of sexual maturity, among other criteria.

Administration of hormones or other chemical compounds may be necessary to prepare the female for egg production, mating, and/or reimplantation of embryos. The type of hormones/cofactors and the quantity used, as well as the timing of administration of the hormones will vary for each species of mammal. Such considerations will be readily apparent to one of ordinary skill in the art Typically, a primed female (i.e., one that is producing eggs that can be fertilized) is mated with a stud male, and the resulting fertilized embryos are then removed for introduction of the transgene(s). Alternatively, eggs and sperm may be obtained from suitable females and males and used for in vitro fertilization to produce an embryo suitable for introduction of the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method is to incubate the embryos in vitro for about 1–7 days, depending on the species, and then reimplant them into the surrogate host.

Reimplantation is accomplished using standard methods. The female "foster mother" strain to be used is selected for general hardiness and health, and for her ability to care for the offspring. In the case of mice, strains such as C57BL/6×DBA1 or CD1 are suitable. Usually, the surrogate host is anesthetized, and the embryos are inserted into the oviduct. The number of embryos implanted into a particular host will vary by species, but will usually be comparable to the number of offspring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue (about 1 cm is removed from the tip of the tail) and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular markers or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic mammals may be obtained by mating the transgenic mammal with a suitable partner, or by in vitro fertilization of eggs and/or sperm obtained from the transgenic mammal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

Preparation of Knockout/Transgenic Mammals

Mammals containing more than one knockout construct and/or more than one transgene are prepared in any of several ways. The preferred manner of preparation is to generate a series of mammals, each containing one of the desired knockout constructs or transgenes. Such mammals are bred together through a series of crosses, backcrosses and selections, to ultimately generate a single mammal containing all desired knockout constructs and/or transgenes, where the mammal is otherwise congenic (genetically identical) to the wild type except for the presence of the knockout(s) constructs and/or transgene(s).

Typically, crossing and backcrossing is accomplished by mating siblings or a parental strain with an offspring, depending on the goal of each particular step in the breeding process. In certain cases, it may be necessary to generate a large number of offspring in order to generate a single offspring that contains each of the knockout constructs and/or transgenes in the proper chromosomal location. In addition, it may be necessary to cross or backcross over several generations to ultimately obtain the desired genotype.

Uses of Knockout Mammals

The mammal of this invention will have a variety of uses depending on the gene or genes that have been suppressed. Where the gene or genes suppressed encode proteins believed to be involved in immunosuppression or inflammation, the mammal may be used to screen for drugs useful for immunomodulation, i.e., drugs that either enhance or inhibit these activities. Screening for useful drugs would involve administering the candidate drug over a range of doses to the mouse, and assaying at various time points for the immunomodulatory effect(s) of the drug on the immune disorder being evaluated. Such assays would include, for example, looking for increased or decreased T and B cell levels, increased or decreased immunoglobulin production, increased or decreased levels of chemical messengers such as cytokines (e.g., interleukins and the like), and/or increased or decreased levels of expression of particular genes involved in the immune response.

For example, patients undergoing chemotherapy often experience immunosuppression. It would be desirable to activate the immune system of such individuals by administering to the patient a therapeutic agent capable of producing such an effect. A mammal of the present invention could be used to screen a variety of compounds, either alone or in combination, to determine whether partial or total restoration or activation of the immune response results.

The same strategy could be applied to find compounds that would be useful in suppressing the inflammatory response observed in many patients with arthritis, or useful in suppressing the autoimmune phenomenon observed in patients with rheumatoid arthritis and lupus.

In addition, mammals of the present invention can be useful for evaluating the development of the immune system, and for studying the effects of particular gene mutations.

Uses of Transgenic/Knockout Mammals

The transgenic/knockout mammal and its progeny of this invention will have a variety of uses depending on the transgene.s expressed and the knockout constructs they contain. The mammal may be used to screen for drugs or a therapeutic regimen useful for prophylactic or therapeutic treatment of diseases such as sepsis or other immunological disorders. Screening for a useful drug would involve first inducing the disease in the mammal (i.e., exposing the mammal to a pathogen or toxin causing sepsis) and then administering the candidate drug over a range of doses to the mammal, and assaying at various time points for the effect(s) of the drug on the disease or disorder being evaluated. Alternatively, or additionally, the drug could be administered prior to or simultaneously with exposure to induction of the disease.

In addition to screening a drug for use in treating a disease or condition, the mammal of the present invention could be useful in designing a therapeutic regimen aimed at preventing or curing the disease or condition. For example, the mammal might be treated with a combination of a particular diet, exercise routine, radiation treatment, and/or one or more compounds or substances either prior to, or simultaneously, or after, the onset of the disease or condition. Such an overall therapy or regimen might be more effective at combating the disease or condition than treatment with a compound alone.

Assays to evaluate the efficacy of the compound and/or therapeutic regimen would include, for example, looking for increased or decreased T and B cell levels, increased or decreased immunoglobulin production, increased or decreased levels of chemical messengers such as cytokines (e.g., tumor necrosis factor and the like), and/or increased or decreased levels of expression of particular genes involved in the immune response. In addition, such criteria as blood pressure, body temperature, body weight, pulse, behavior, appearance of coat (ruffled fur) and the like could be evaluated.

In addition, mammals of the present invention can be useful for evaluating the development of the immune system, and for studying the effects of particular gene mutations.

The transgenic knockout mammals of this invention may also be used to generate one or more cell lines. Such cell lines have many uses, as for example, to evaluate the effect(s) of the transgene knockout on a particular tissue or organ, and to screen compounds that may affect the level of activity of the transgene in the tissue. Such compounds may be useful as therapeutics to modulate the activity of the transgene.

Production of such cell lines may be accomplished using a variety of methods, known to the skilled artisan. The actual culturing conditions will depend on the tissue and type of cells to be cultured. Various media containing different concentrations of macro and micro nutrients, growth factors, serum, and the like, can be tested on the cells without undue experimentation to determine the optimal conditions for growth and proliferation of the cells. Similarly, other culturing conditions such as cell density, media temperature, and carbon dioxide concentrations in the incubator can also readily be evaluated. repair, and identifying compounds that affect this process.

Other uses will be readily apparent to one of skill in the art.

The invention will be more fully understood by reference to the following examples. These examples are not to be construed in any way as limiting the scope of this invention.

EXAMPLE I

Preparation of a CD28 Knockout Mouse

1. Preparation of Knockout DNA Construct

A genomic clone of the murine CD28 gene (described by-Lee et al., *J. Immunol.*, 145:344 [1990]) was isolated from a murine BALB/c genomic library using the murine CD28 exon 2 cDNA sequence as a probe. The 3' end of intron 1 and the 5' region of exon 2 were replaced by inserting a DNA construct encoding the neomycin resistance gene (neo) linked to the herpes simplex virus thymidine kinase promoter. The neo DNA construct was obtained from the plasmid pMCIneoPolA (Thomas et al., *Cell*, 51:503 [1987]) by digestion of this plasmid with restriction endonucleases XbaI and EcoRI. The neo sequence was ligated into the genomic CD28 sequence by cutting the genomic sequence with EcoRI and XbaI, and this neo/CD28 knockout construct was then ligated into the vector pGEM7 (Promega Corp. Madison, Wis.). This vector was transformed into the *E. coli* bacteria strain DH5 alpha for amplification. After amplification, the plasmid was purified using the standard alkaline lysis and CsCl gradient for purification.

2. Electroporation and Injection of Stem Cells

The purified plasmid knockout construct was linearized by digestion with restriction nuclease AatII thereby generating a shorter arm and a longer arm of CD28 sequence on either side of the neo gene. The linearized knockout construct was then transfected into the embryonic stem cell line D3 as follows: About 5 nmol of linearized DNA was added to about $5 \times 10^6$ ES cells in a volume of about 800 $\mu$l of culture media. The cells were pulsed at 0.34 kilovolts and 250$\mu$F, and each vial of cells was then plated on to two 10 cm cell culture plates containing embryonic fibroblast feeder cells, and precoated with 1 percent gelatin, and containing 10 ml DMEM medium (Gibco/BRL, Grand Island, N.Y.), 15 percent fetal calf serum (Gibco/BRL, Grand Island, N.Y. or equivalent from Hyclone Labs, Logan, Utah), and leukemia inhibitory factor (Fung-Leung et al. *Cell*, 65:443–449 [1991]). After two days, neo selection was started by adding the antibiotic G418 at 250 $\mu$g/ml to the cultures. Cells that survived in the presence of G418 most likely contained the knockout construct. These cells were then screened to verify that the cells that had incorporated the knockout construct in the genomic DNA. Screening was accomplished using the polymerase chain reaction (PCR) method for DNA amplification. Two primers were used in PCR. The first primer was directed to a sequence specific for the thymidine kinase promoter and is set forth below; the second primer, also set forth below, was specific for intron 2 of CD28.

Primer 1 (SEQ ID NO:1):
5'-CCTGAGTCCTGATCTGTCAGACT-3'
Primer 2 (SEQ ID NO:2):
5'-ATTCGGCAATGACAAGACGCTGG-3'

The D3 cell line containing the CD28 knockout construct has been deposited with the ATCC (American Type Culture Collection) as accession number CRL 11382.

Southern blots of genomic DNA from control and transfected cells were analyzed to assess transfected cells that contained the knockout construct in the proper location and orientation in genomic DNA, (i.e., to identify those cells that had undergone homologous recombination). The Southern blots were probed with two probes. The first probe was a 200 base pair (bp) EcoRI/XbaI fragment of CD28 intron 2. The second probe was a fragment of the neo gene and was generated by digesting the plasmid pMClNeoPolA (described above) with HindIII and XhoI, and isolating the 1.2 kb fragment using standard agarose gel electrophoresis procedures.

Cell lines containing the CD28-neo insert that had inserted into the genomic DNA properly were prepared for injection into murine embryos by trypsin treatment following methods described by Robertson (*Teratocarcinomas and Embryonic Stem Cells: A Practical Approach*, IRL Press, Washington, D.C., [1987], Robertson, E. J., ed). The embryos injected were 3.5 day old embryos obtained by perfusing the uterus of female mice that had been mated with male mice. After injection of the embryonic stem cells into the embryos, the embryos were implanted into pseudopregnant female mice for gestation. The offspring were either mated to each other or with a mouse with suitable coat color so as to be able to detect mice carrying the knockout construct.

3. Screening Mice for Knockout Construct

The offspring of these matings were evaluated for the presence of the knockout construct by probing a Southern blot of DNA obtained from tail tissue with the neo gene probe (described above). The probe did not hybridize with DNA obtained from the wild type mice.

To evaluate the level of CD28 expression in knockout and wild type mice, peripheral blood lymphocytes (PBLs) were obtained from these mice by collecting about 25 μl of blood from tail bleeds into a tube containing 100 μl of 20 mM EDTA in phosphate buffered saline (PBS). PBLs were isolated by adding 2 ml of Gey's lysis buffer (to lyse red blood cells) to the blood solution and washing twice with PBS supplemented with 1 percent BSA (bovine serum albumin) and 0.1 percent sodium azide. The cells were incubated with phycoerythrin (PE) conjugated hamster anti-murine CD28 monoclonal antibody (5 μl of a solution of 0.2 mg/ml) obtained from Pharmingen (San Diego, Calif.). The PBLs were then fixed with 1 percent paraformaldehyde. About 5,000 cells were analyzed for each mouse. These cells were then sorted based on PE intensity using FACS (fluorescence activated cell sorting; a Becton-Dickinson [Mountain View, Calif.] FACS machine was used).

4. Analysis of Effects of Knockout Gene

The thymocyte populations of homozygous knockout mice and wild type mice were evaluated for cell surface CD4 and CD8 expression. Thymocytes were stained with FITC-coupled monoclonal antibody directed to CD8, or with phycoerythrin-coupled monoclonal antibody directed to CD4 (antibodies were obtained from Beckton-Dickinson, Mountain View, Calif.). Splenocytes were evaluated for expression of the cell surface marker B7 and the amount of B cells by staining with FITC-labeled anti B220 and biotin-labeled anti B7 antibody that was detected with PE-labeled streptavidin. The cells were analyzed by FACS, and about 10,000 cells were analyzed for each sample. All mice showed normal CD4/ CD8 subtypes in the thymus, suggesting that T cell development was not detectably affected in the knockout mice. In addition, all mice showed a similar B cell and B7 profiles, suggesting that the knockout mice did not compensate for the mutation by altering the level of B7 expression.

Figure 2:
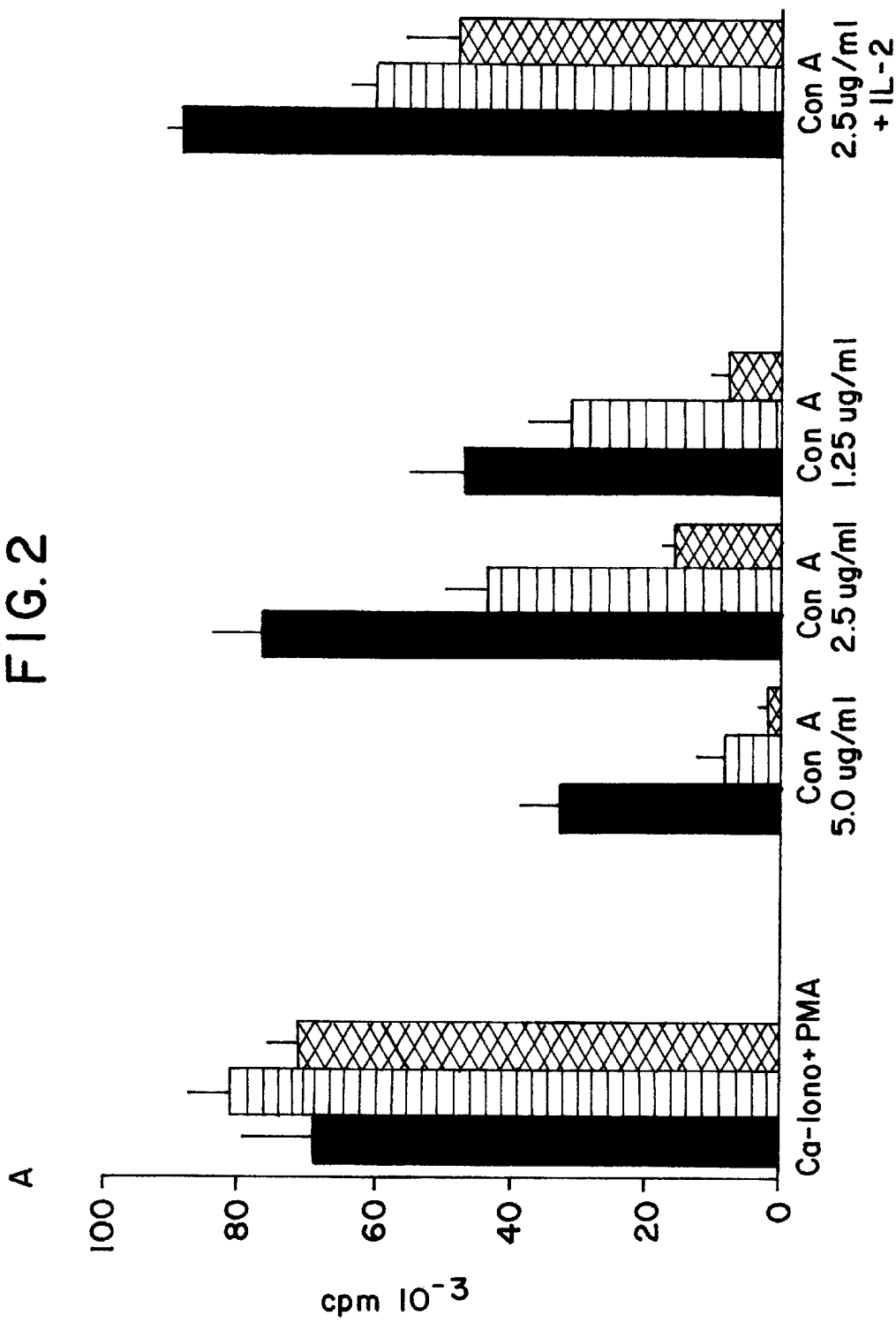
FIG. 2 depicts the effects of the CD28 knockout construct on splenocyte proliferation of 1) the calcium ionophore in combination with PMA, and 2) Concanavalin A (in the presence or absence of IL-2). Solid black bars represent splenocytes from wild type mice, horizontally hatched bars represent splenocytes from heterozygous knockout mice, and cross hatched bars represent splenocytes from homozygous knockout mice. These results were obtained after two days of culturing the cells.

The immune responses of wild type, heterozygous, and homozygous knockout mice were evaluated by assaying splenocytes from each type of mouse for proliferation when exposed to various mitogens. Splenocytes were obtained by sacrificing a mouse and extracting its spleen. The spleen was mashed in media containing 2 percent fetal calf serum, and the red blood cells were lysed as described above. These cells were then plated into 96 well flat bottom plates at a density of about $2 \times 10^5$ cells/well, and various mitogens were added as follows: 1) Concanavalin A (ConA) was evaluated at concentrations between 5.0 μg/ml and 1.25 μg/ml, and at 2.5 μg/ml in either the presence or absence of IL-2; and 2) the calcium ionophore A23167 at 250 ng/ml was evaluated in the presence of the phorbol ester PMA at 50 ng/ml. Cell proliferation was determined by measuring $^3$H-thymidine uptake after two days of culturing. The results are shown in FIG. 2. With respect to ConA, cells from the wild type mice showed a large proliferative response, cells from the heterozygous CD28 knockout mice showed less of a response, and cells from the homozygous CD28 knockout mice had the lowest amount of $^3$H-thymidine uptake. However, the response to the calcium ionophore/PMA was more comparable between the three types of cells.

Figure 3:
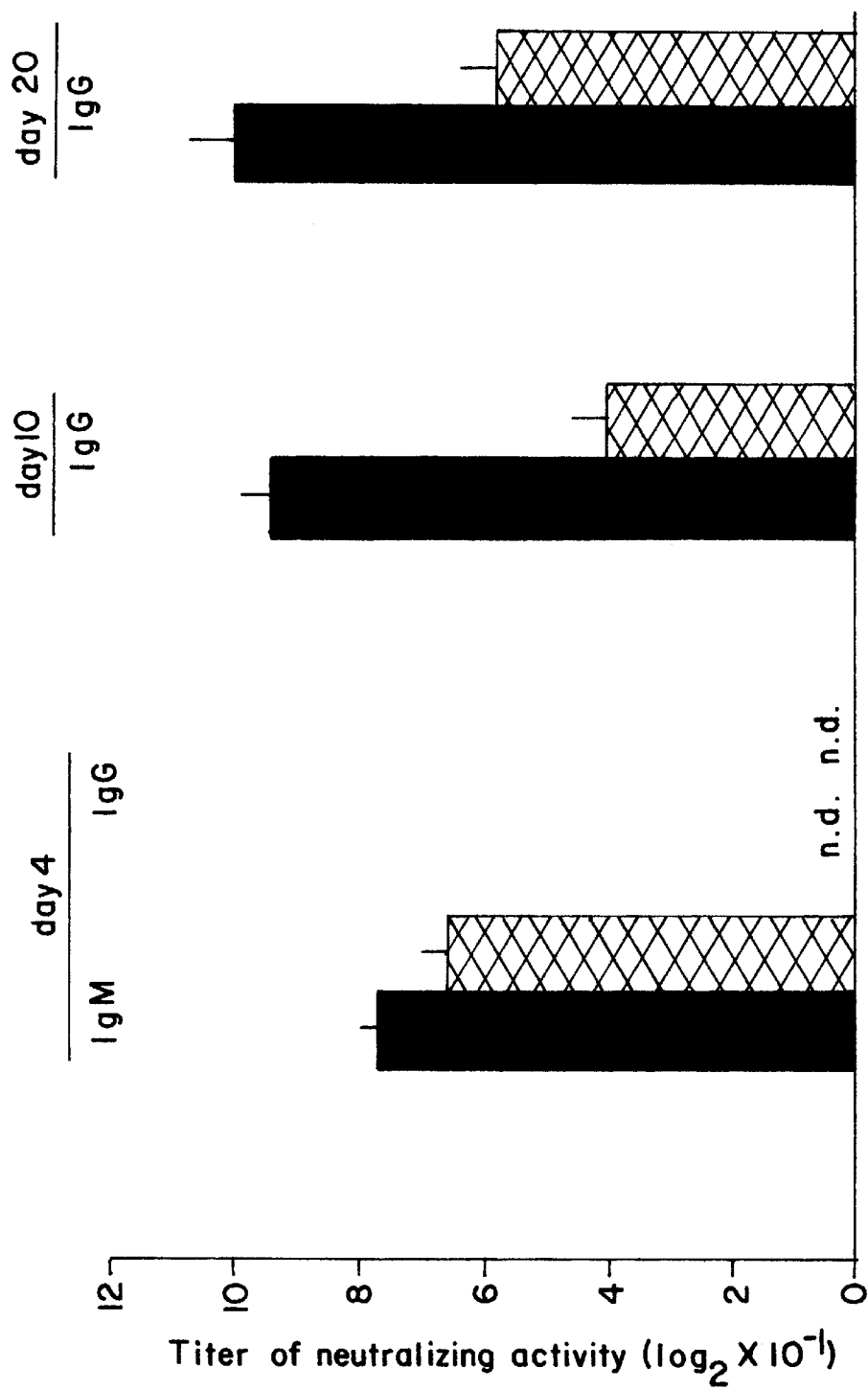
FIG. 3 depicts the level of neutralizing IgM and IgG antibodies in wild type (solid bars) and homozygous CD28 knockout mice (cross hatched bars) immunized with vesicular stomatis virus. Data were collected at various times (as indicated) after immunization. "n.d." indicates no detectable level.

The presence of neutralizing antibodies in the sera in response to infection with vesicular stomatis virus (VSV, Indiana strain) was evaluated. Mice were injected with $2 \times 10^6$ pfu of the virus. After 4, 10, or 20 days, sera from the mice were analyzed for neutralizing IgM and IgG antibodies using methods described by Leist et al. (*J. Immunol.*, 138:2278 [1987]). The results, expressed as titers of neutralizing activity, are shown in FIG. 3. Each bar represents the mean value for a group of 5 mice; n.d. means "not detectable". While titers of homozygous knockout and wild type mice were comparable at day 4, the homozygous knockout mice had much lower levels of IgG than the wild type mice at days 10 and 20.

EXAMPLE 2

Prepartion of a CD45 Knockout Mouse

1. Preparation of DNA Knockout Construct

Figure 4:
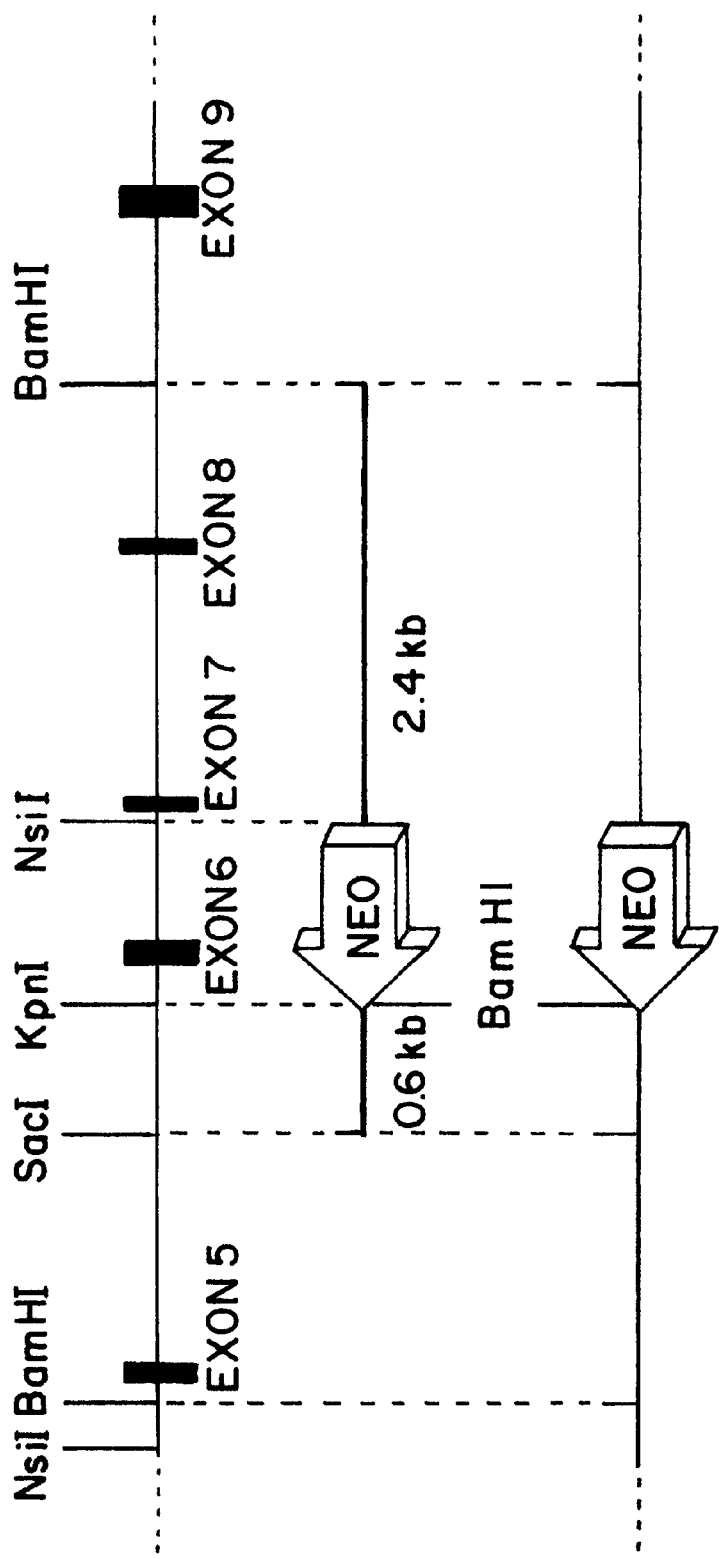
FIGS. 4 (A–C) depicts the DNA knockout construct used to suppress expression of CD45 exon 6 isoform. 4A depicts a portion of the native CD45 gene. 4B depicts the knockout construct where exons 6–8 have been replaced with the neo sequence. 4C shows the restriction sites of the knockout construct.

A 4.0 kb genomic murine DNA fragment of the CD45 gene was isolated as described by Johnson et al. (*J. Biol. Chem.*, 264:6220–6229 [1989]) This fragment spans exons 6–8 of the gene. The fragment was inserted into the vector pGEM-9Zf(–) (Promega Corp., Madison, Wis.) previously digested with restriction endonucleases SacI and BamHI. After insertion, the construct was digested with restriction endonucleases KpnI and NsiI; these sites are located between introns 5 and 6, and between introns 6 and 7, respectively of the CD45 gene fragment. The neomycin resistance gene construct containing a poly-A termination signal was obtained from the plasmid pMCIneoPolA (Thomas et al., *Cell*, 51:503 [1987]) and was digested with KpnI and NsiI and was then ligated into the construct in the antisense orientation relative to the CD45 transcriptional orientation. The resulting knockout construct is depicted in FIG. 4.

2. Electroporation and Injection of Stem Cells

The knockout construct was linearized by digestion with restriction endonuclease SacI, and about 25 μg of this DNA was electroporated into D3 embryonic stem cells. The electroporated cells containing the construct have been deposited with the ATCC as accession number CRL 11381. Electroporation was accomplished using the procedure described in Example 1. About 50 μg DNA per $10^7$ cells was used. After electroporation, the cells were plated and screened as described in Example 1.

Cells that were resistant to G418 were screened for homologous recombination by PCR using primers specific for the neomycin resistance gene and for a site specific to the CD45 gene. The primers used are set forth below:

Primer 1 (SEQ ID NO:3)
5'-CTTACTACACATCCCAACCT-3'
Primer 2 (SEQ ID NO:4):
CTTGACGAGTTCTTCTGAGG-3'

PCR reaction conditions were: denaturing at 91° C., annealing at 60° C., and extension at 72° C. About 35–40 cycles were conducted. In addition, homologous recombination in these cells was confirmed by Southern blotting analysis using a $^{32}$P labeled 1.4 kb DNA probe spanning a region between introns 4 and 5 of the CD45 gene. Southern blotting was conducted by isolating genomic DNA from G418 resistant cells using standard methods as described by Sambrook et al (*Molecular Cloning: A Laboratory Manual*, Cold Spring Harbor Laboratory Press, Cold Spring Harbor, N.Y. [1989]). The genomic DNA was digested with BamHI, separated using standard agarose electrophoresis, and blotted on to Immobilon-N membrane paper. Transfer to the membrane was done at 20° C. for 12 hours in 10 percent SSC (Sambrook et al., supra). The membrane was probed for 12 hours at 67° C., and then washed three times. The first wash was 5 percent SSC, 0.01 percent SDS; the second wash was 3 percent SSC, 0.01 percent SDS; the third wash was 1 percent SSC, 0.01 percent SDS.

Preparation of ES cells, injection into embryos, and implantation into foster mothers was as described in Example 1.

3. Screening Mice for Knockout Construct

Offspring (the founder mice) were screened for mosaicism by evaluating fur pigmentation (the embryo was from a black fur mouse and the embryonic stem cell was from an agouti mouse; most mosaic mice therefore had a coat that was partially agouti and partially black). The founder mice were back crossed to generate heterozygous CD45 knockout mice. Offspring from this cross were screened to determine whether they were heterozygous or homozygous for the CD45 knockout construct. Screening was done by Southern blotting of DNA obtained from tail tissue. The tail tissue was obtained by cutting off a piece of the tail of 3 week old mice. The tail tissue was incubated with 500 μl of a solution of TNE (Sambrook et al., supra), 150 μg/ml Proteinase K, 1 percent SDS, and 1 mg/ml Pronase E. After this incubation, 750 μl of this solution was added to 750 μl of phenol:chloroform (1:1 v/v) to isolate the DNA. The mixture was centrifuged 5 minutes to pellet cellular debris. The supernatant was added to 450 μl of isopropyl alcohol and this mixture was incubated on dry ice to precipitate the DNA. After incubation, the precipitated DNA was pelleted by centrifugation, air dried, and resuspended in 100 ;μl of distilled water, and kept at 4° C. Southern blots of this DNA were done as described above for the embryonic stem cells.

To test the B cells and T cells of the mice for expression of CD45 and to determine the zygosity of the mice, cells from various mice were screened for the presence of immunological markers using antibodies and methods as described below.

Single cell suspensions of thymocytes, splenocytes, mesenteric lymph node cells and bone marrow cells from 6–12 week old mice were prepared as follows: Mice were sacrificed using carbon dioxide following standard protocols of the Canadian Research Council, and organs were harvested from each mouse and kept in phosphate buffered saline (PBS) at 4° C. Single cell suspensions were prepared by grinding the organs against a steel screen mesh with a syringe plunger. The cells were washed twice in PBS. Each suspension was resuspended in PBS and incubated with the appropriate antibodies as follows:

1) Pan-CD45 antigen was detected with either 1) FITC (fluorescein isothiocyanate) or PE (phycoerythrin) labeled Ly-5 monoclonal antibody (Pharmingen, San Diego, Calif.) or 2) with rat the IgG monoclonal antibody 13/2.3 derived from supernatant (Trowbridge et al., *J. Exp. Med.*, 148:313 [1978]).

2) The CD45-exon 4 encoded epitope was detected with rat monoclonal antibody 14.8 derived from supernatant; obtained from Kincade et al., *J. Immunol.*, 127:2262–2268 [1981]).

3) The CD45-exon 5 encoded epitope was detected with rat IgG monoclonal antibody MB23G2 obtained from supernatant (Birkeland et al., *Proc. Natl. Acad. Sci. USA*, 86:6734–6738 [1989]).

4) A CD45 glycosylation epitope of B cells was detected with monoclonal antibody B220 (FITC or PE labeled; Pharmingen, San Diego, Calif.).

5) CD4 was detected with anti-CD4 monoclonal antibody (FITC or PE labeled) obtained from Becton-Dickinson (Mountain View, Calif.).

6) CD8 was detected with anti-CD8 monoclonal antibody (FITC, PE, or biotin labeled) obtained from Becton-Dickinson (Mountain View, Calif.).

7) TCRVbeta8.1+8.2 was detected with KJ16 rat IgG monoclonal antibody (Hoskins et al., *J. Exp. Med.*, 160:452–471 [1984]).

8) TCRVbeta8.2 was detected with mouse IgG monoclonal antibody F23.2 (Staerz et al., *J. Immunol.* 134:3994–4000 [1985]).

9) H-2b was detected with FITC labeled monoclonal antibody B8–24 (Pharmingen, San Diego, Calif.).

10) H-2d was detected with FITC labeled monoclonal antibody 34–2–12 (Pharmingen, San Diego, Calif.)

11) CD3 was detected with anti-CD3 monoclonal antibody (Pharmingen, San Diego, Calif.).

12) Thyl.2 was detected with anti-Thyl.2 FITC or PE labeled monoclonal antibody (Pharmingen, San Diego, Calif.).

13) slgM antigen was detected with FITC labeled monoclonal antibody (Pharmingen, San Diego, Calif.).

Labeling the cells with the antibodies was performed as follows: For single or double staining using PE or FITC labeled antibody, about $1 \times 10^6$ cells were incubated with 4 μl of labeled antibody at 4° C. for 30 minutes in about 100 μl of a solution of Staining Buffer consisting of PBS with 10 percent fetal calf serum (FCS) and 0.1 percent sodium azide. The cells were then washed once in 5 ml PBS and fixed in 1 percent paraformaldehyde (in PBS) and kept at 4° C. until ready for FACS analysis.

For labeling cells using the supernatants, $1 \times 10^6$ cells were incubated with about 50 μl of the appropriate supernatant for 30 minutes at 4° C. in 100 μl Staining Buffer. After this incubation, antibody binding was visualized by incubation with 3 μl of PE or FITC labeled goat anti-mouse IgG, or goat anti-rat IgG (both obtained from Southern Biotechnology Associates, Birmingham, Ala.) for about 30 minutes at 4° C. The cells were then washed once in PBS and then fixed in paraformaldehyde as described above.

Visualization of rat or mouse antibodies was conducted using PE or FITC labeled goat anti-rat IgG and FITC labeled goat anti-mouse antisera (both obtained from Southern Biotechnology Associates, Birmingham, Ala.), and visualization of biotin labeled antibodies was with streptavidin-RED613 (Gibco/BRL, Grand Island, N.Y.). Where double staining protocols with rat antibodies were used, unspecific staining due to remaining anti-rat IgG sites was first blocked using 2 μg/100;1 rat IgG (Sigma Chemical Co., St. Louis, Mo.) and incubating the cells at 4° C. for 10 minutes before washing with PBS. All samples were analyzed with a FACScan machine using a Lysis II program (Becton-Dickinson, Mountain View, Calif.)

The results demonstrated that CD45 exon 6 isoform was not detected on the cell surface of B lymphocytes from bone marrow and spleen of homozygous CD45 exon 6 isoform knockout mice. In addition, the number of peripheral T cells that expressed CD45 exon 6 isoform on the cell surface was significantly reduced as compared with wild type mice. Heterozygous knockout mice had a decreased level of CD45 exon 6 isoform expression on these cells as compared to wild type mice.

The total number of slgM+ cells in the spleen and bone marrow was comparable between homozygous knockout mice and wild type mice. However, the total number of T cells in peripheral lymphoid organs was considerably reduced in the homozygous knockout mice as compared to wild type mice. No significant differences in peripheral T and B cell compartments and bone marrow cells were detected between heterozygous knockout mice and wild type mice even though CD45 was expressed at a reduced level in heterozygous knockout mice as compared to wild type mice.

Although CD45 exon 6 isoform expression on thymocytes was significantly suppressed in homozygous knockout mice as compared to wild type mice, the total number of thymocytes in homozygous knockout mice was only slightly reduced as compared to wild type mice. In addition, homozygous knockout mice had normal numbers of immature CD4+ CD8+ double positive thymocytes, however, the total number of CD4− CD8− precursor cells was increased, and the size of both mature CD4+ and CD8+ T cell lineages was significantly reduced in these mice.

4. Analysis of Effects of Knockout Gene

To examine the effects of CD45 exon 6 isoform gene suppression on B cell development, single cell suspensions of bone marrow, spleen, or peritoneum cells were cloned in semi-solid agar under a variety of conditions that allow selective proliferation of either pre-B cells (IL-7 or IL-7 plus the stroma cell line S17), B cells (LPS or LPS+S17) or myeloid cells (IL-3 or L929 conditioned medium as a source of macrophage colony stimulating factor M-CSF-1). To evaluate proliferation, double layer agar cultures were established as follows: first, a 1 ml-underlayer consisting of OPTI-MEM medium (Gibco/BRL, Grand Island, N.Y.) supplemented with 2.4 g/l $NaHCO_3$, 5 mg/l streptomycin, $5 \times 10^3$ u/l penicillin, $5 \times 10^{-5}$ M beta-mercaptoethanol, 10% fetal calf serum (Gibco/BRL, Grand Island, N.Y.) and 0.3% melted Bacto agar (Difco Labs) was prepared. Next, the S17 stromal cells (Collins et al., *J. Immunol* 138: 1082–1087 [1987]) were allowed to adhere to the plastic plate for 5 hours ($2 \times 10^4$ irradiated [2000Gy] S17/plate). Nonadherent cells were then removed by vacuum suction, and the bottom agar layer containing the appropriate supplements was poured.

The media was supplemented with either LPS at 25 μg/ml (lipopolysaccharide from *Salmonella typhosa* strain W0901; Difco Labs); murine IL-7 and IL-3 (added to the media as culture supernatants from cell lines containing the appropriate vectors; described in detail by Cumano et al., *Eur. J. Immunol.*, 20:2183–2189 [1990]; Cumano et al., *EMBO J.*, 11:593–601 [1992]; Karasuyama et al., *Eur J. Immunol.* 18:97–104 [1988]); or macrophage-colony stimulating factor (M-CSF-1; obtained from L929 conditioned medium). Optimal amounts of IL-3, IL-7 and M-CSF were determined in titration experiments as described by Cumano et al., supra.

The results are shown in Table 4 as the absolute numbers of colony forming cells found in different tissues tested. There was no detectable difference in the amount of colony formation of bone marrow derived myeloid or B-cell progenitors between homozygous knockouts, heterozygous knockouts and wild type mice.

TABLE I

Total Number of Lymphoid Cells (× $10^8$)

| Cells & Stimulus | Wild-type | Heterozygotes | Homozygotes |
|---|---|---|---|
| Bone Marrow | | | |
| IL-7 | 27 ± 5 | 23 ± 2 | 30 ± 8 |
| LPS | 40 ± 6 | 33 ± 3 | 42 ± 12 |
| S17 + IL-7 | 52 ± 13 | 47 ± 15 | 54 ± 20 |
| S17 + LPS | 55 ± 16 | 50 ± 13 | 53 ± 21 |
| IL-3 | 23 ± 3 | 18 ± 1 | 21 ± 5 |
| M-CSF-1 | 28 ± 9 | 29 ± 9 | 37 ± 16 |
| Spleen | | | |
| S17 + LPS | 127 ± 47 | 140 ± 41 | 150 ± 24 |
| Peritoneum | | | |
| S17 + LPS | 50 ± 6 | 52 ± 3 | 52 ± 3 |
| Fetal Liver | | | |
| S17 + LPS | ND | 13 ± 4 | 13 ± 7 |

To determine the importance of CD45 exon 6 isoform expression on immunoglobulin (Ig) mediated cell signaling effects, the anti-Igμ specific monoclonal antibody B-76 (obtained from Dr. Michael Julius, McGill University, Montreal, Canada) was added to splenic B cells obtained from homozygous and heterozygous knockout mice as well as wild type mice. Splenic B cells were placed in microtiter plates at a density of about 105 cells/well and incubated for 3, 4, or 5 days in an atmosphere of 5 percent CO2 at 37° C. with either no exogenous stimulant added, or lipopolysaccharide or antibody B-76 added. Stimulation was measured by adding $^3$H-thymidine to the cells for 10 hours using 1 μCi of $^3$H-thymidine per well. The contents of each well was then blotted on to filter paper and counted for radioactivity.

The results, shown in FIG. 5, indicated that anti-Igμ stimulation requires CD45 exon 6 isoform expression on B cells whereas LPS stimulation does not.

To evaluate T cell effector functions in vivo, homozygous and heterozygous knockout mice were tested for their ability to generate an antiviral cytotoxic T cell response. About 30 μl of lymphocytic choriomeningitis virus Armstrong (LCMV) equivalent to about 400 pfu was injected subcutaneously into the hind footpads of the mice. Swelling of the footpad was measured daily with a spring loaded caliper. The results are shown in FIG. 6A. The early phase of the swelling reaction (days 7–9 after infection) was completely abrogated in homozygous knockout mice (open triangles) but not in wild-type mice (closed triangles).

To further confirm the inability of homozygous knockout mice to generate a cytotoxic response to certain pathogens, cytotoxic lymphocytes were obtained from spleens of mice after the mice had been infected with LCMV. These cytotoxic lymphocytes were then restimulated in vitro 5 or 30 days after the initial infection. Restimulation was accomplished by exposure to LCMV infected peritoneal macrophages (Lehmann-Grube, *Virol. Monogr.*, 10 [1971]) prepared as follows: macrophages were obtained by washing the peritoneum of C57BL/6 mice which had been injected six days earlier with 2 ml of thioglycolic acid (3 percent wt/vol.) and were infected intraperitoneally four days earlier with 1000 pfu LCMV Armstrong.

Cultures were established with $4 \times 10^6$ responder spleen cells and $2 \times 10^5$ LCMV infected irradiated (1200 rads) peritoneal macrophages. The cultures were incubated for 5 days in IMDM medium with 10 percent fetal calf serum and $10^{-5}$ M beta-mercaptoethanol. Duplicate dilutions of the cultures were assayed for LCMV specific T cell cytotoxicity on LCMV infected $^{51}$Cr labeled MC57(H-2b) fibrosarcoma target cells according to standard protocols described by Cerrottini et al. (*Adv. Immunol.*, 18:67–132 [1974]). Specific lysis after four hours was then calculated as described by Cerrottini et al., supra.

Figure 6B:
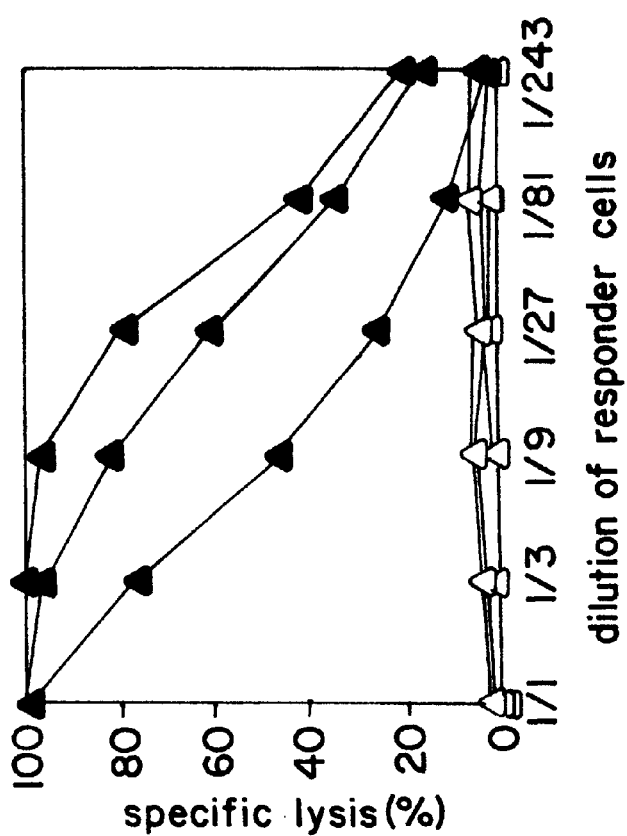
FIGS. 6(A–B) depicts the cytotoxic T cell response of wild type and CD45 exon 6 isoform homozygous knockout mice when exposed to LCMV (lymphocytic choriomeningitis virus strain Armstrong). 6A depicts the footpad swelling reaction, and 6B depicts specific lysis of LCMV infected cells. Open triangles represent the homozygous CD45 exon 6 isoform knockout mice, and closed triangles represent the wild type mice.
Figure 6A:
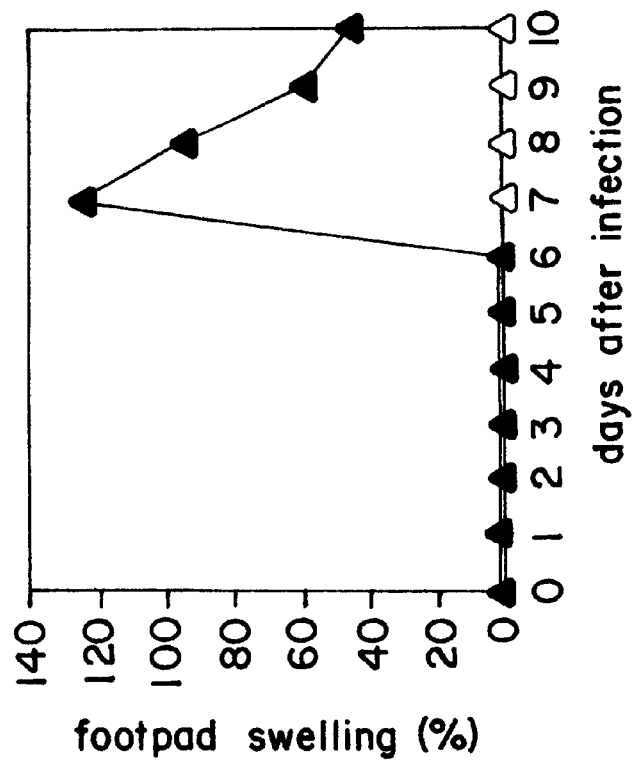

The results, shown in FIG. 6B, indicate that homozygous knockout mice (open triangles) were unable to mount a cytotoxic response, while wild-type mice (closed triangles) were able to mount such a response.

EXAMPLE 3

Preparation of a CD45 Transgenic Mouse

1. Preparation of Transgene Cassette

The murine cDNA encoding the CD45RO isoform (CD45 gene not expressing exons 4–6) containing the full-length coding sequence as well as about 70 bases of 5' untranslated and about 300 bases of 3' untranslated sequence, was obtained from a murine lymphocyte library, and isolated as an approximately 3.5 kb SalI-SalI fragment. This fragment was inserted into the BamHI cloning site of the expression vector p1017 described by Chaffin et al. (*EMBO J.*, 9:3821–3829 [1990]). The vector p1017 contains an approximately 3.2 kb thymocyte specific murine lck promoter (Garvin et al., *Int. Immunol.*, 2:173–180 [1990]) inserted between the EcoRI and SmaI sites of the cloning vector pUC19 (Stratagene, La Jolla, Calif., or equivalent). In addition, the p1017 contains a polylinker region adjacent to the lck promoter and an approximately 2.1 kb human growth hormone gene (hGH) sequence (extending from the BamHI site in exon 1 to the EcoRI site downstream of the poly-A sequence [Seeberg, DNA 1:239–249 1982]) adjacent to the other end of the polylinker sequence.

The final vector containing the CD45RO transgene was amplfied in *E coli* cells using standard procedures and purified using the standard miniprep method (Sambrook et al., supra). The DNA cassette containing the promoter, transgene, and hGH sequence, as shown in FIG. 7, was isolated by restriction endonuclease digestion with Not., and purified by agaraose gel electrophoresis.

2. Insertion of Transgene Cassette into Mice

The purified CD45RO DNA cassette was microinjected into C57BL/6 xDBA F2 embryos using standard procedures as set forth by Hogan et al., supra. The embryos were implanted into foster mothers The offspring (founder mice) were screened for the presence of the transgene by Southern blot analysis of DNA derived from mouse tail tissue. The probe for the Southern blot analysis consisted of the 3' region of the hGH gene.

To establish transgenic lines with either the H-2b or H-2d background, the founder mice were crossed with either C57BL/6 or DBA/2 mice for five generations.

EXAMPLE 4A CD45

Knockout, Transgenic Mouse

A C57BL/6 CD45RO transgenic mouse (homozygous wild-type for the CD45 exon 6 isoform) was crossed with the CD45 exon 6 knockout mouse (described in Example 2) to generate F1 offspring that contained the CD45RO transgene and were heterozygous for the CD45 exon 6 isoform knockout construct. These mice were backcrossed to homozygous CD45 exon 6 knockout mice to generate offspring that contained the transgene and were either heterozygous or homozygous for the CD45 exon 6 knockout construct. CD45 exon 6 knockout heterozygotes and homozygotes were distinguished by digesting DNA obtained from tail tissue (as described in Examples 1 and 2) with the restriction enzyme PvuII, Southern blotting this DNA, and probing the blot with wild-type full-length CD45 cDNA.

The mice found to be homozygous for the CD45 exon 6 knockout construct (but containing the CD45RO transgene) were analyzed for the effects of the transgene on T cell maturation and activity. All analyses of mice were conducted using two littermates of each genotype as replicates, and all mice were approximately four weeks old. In the Tables that follow, the control mice are referred to as "wild type" and contain no knockout or transgene constructs; the mice containing the CD45 exon 6 knockout construct are referred to as "CD45 exon 6 KO"; the mice containing the CD45 exon 6 knockout construct and the CD45RO transgene are referred to as "CD45RO/KO".

The maturation of thymocytes was evaluated in mice of the genotypes listed above. Mice were sacrificed and the thymus of each mouse was removed. Thymocyte suspensions were prepared as described in Example 2, and the thymocytes were then labeled with antibody specific for CD4 or CD8 (as described in Example 2). The results are shown in Table II.

TABLE II

| Relative Percent of T Cell Population In The Thymus | | | |
|---|---|---|---|
| Mouse Genotype | CD4+/8+ | CD4+ | CD8+ |
| Wild Type | 86.1 | 10.7 | 1.7 |
|  | 87.5 | 7.6 | 1.3 |
| CD45 exon 6 KO | 88.4 | 3.6 | 1.0 |
|  | 84.6 | 2.5 | 0.5 |
| CD45RO/KO | 73.4 | 16.5 | 1.4 |
|  | 46.3 | 44.3 | 6.0 |

As can be seen, the relative levels of CD4+ and CD8+ T cells in the CD45 exon 6 knockout mice were much lower than for th wild type or CD45RO genotypes.

Next, the various CD45 genotypes of mice were evaluated for the relative of different types of T cells in the lymph nodes. Mice were sacrificed, and the lymph nodes were removed. T cells were obtained from the lymph nodes as described in Example 2. The T cells were then incubated with anti-CD4 and anti-CD8 antibodies, as described in Example 2. The results are shown in Table III.

TABLE III

| Relative Percent of T Cell Population In The Lymph Nodes | | |
|---|---|---|
| Mouse Genotype | CD4+ | CD8+ |
| Wild Type | 51.8 | 31.7 |
|  | 45.6 | 37.3 |
| CD45 exon 6 KO | 19.9 | 3.8 |
|  | 6.2 | 1.4 |
| CD45RO/KO | 41.6 | 20.7 |
|  | 35.0 | 15.8 |

As is apparent, the CD45 RO transgene ilncreased the level of CD4+ and CD8+ cells as conpared to the CD45 exon 6 knockout.

The relative populaltion of CD4 and CD8 T cells in the spleen were assauled baly extracting the spleens from mice that had been sacrificd, and preparing splenocytes as described in Example 2. The splenocytes were then incubated with anti-CD4 and anti-CD8 antibodis according to the procedure described in Example 2. The results are shown in Table IV.

TABLE IV

Relative Percent of T Cell Population In The Spleen

| Mouse Genotype | CD4+ | CD8+ |
| --- | --- | --- |
| Wild Type | 27.1 | 17.6 |
|  | 22.5 | 13.9 |
| CD45 exon 6 KO | 0.9 | 0.1 |
|  | 0.7 | 0.2 |
| CD45RO/KO | 0.7 | 0.2 |

TABLE IV-continued

Relative Percent of T Cell Population In The Spleen

| Mouse Genotype | CD4+ | CD8+ |
| --- | --- | --- |
|  | 2.0 | 0.5 |

The data indicate that the levels of CD4+ and CD8+ were significantly lower in both the knockout and knockout/transgene mice as compared to the wild type.

All literature cited herein is specifically incorporated by reference.

We claim:

1. A mutant mouse wherein its endogenous CD45 gene has been disrupted using a DNA construct comprising exons 6–8 of the CD45 gene, wherein a marker sequence has been substituted for at least intron 6 and exon 6, and wherein disruption prevents expression of CD45 on B-cells and T-cells and results in a decreased cytotoxic T-cell response.

2. The mutant mouse of claim 1 wherein the marker sequence is the neo DNA sequence.

3. The mouse of claim 1 that further contains a transgene, wherein the transgene comprises a nucleotide sequence encoding the CD45RO isoform.

4. The mutant mouse of claim 3 wherein the marker sequence is the neo DNA sequence.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 23 base pairs
      (B) TYPE: Nucleic Acid
      (C) STRANDEDNESS: Single stranded
      (D) TOPOLOGY: Linear (xi) SEQUENCE DESCRIPTION: SEQ ID NO:1:

CCTGAGTCCT GATCTGTCAG ACT      23

(2) INFORMATION FOR SEQ ID NO:2:

(i) SEQUENCE CHARACTERISTICS:
      (A) LENGTH: 23 Base pairs
      (B) TYPE: Nucleic acid
      (C) STRANDEDNESS:Single stranded
      (D) TOPOLOGY: Linear (xi) SEQUENCE DESCRIPTION: SEQ ID NO:2:

ATTCGGCAAT GACAAGACGC TGG      23

(2) INFORMATION FOR SEQ ID NO:3:

(i) SEQUENCE CHARACTERISTICS:
      (A) LENGTH: 20 Base pairs
      (B) TYPE: Nucleic acid
      (C) STRANDEDNESS: Single stranded
      (D) TOPOLOGY: Linear (xi) SEQUENCE DESCRIPTION: SEQ ID NO:3:

CTTACTACAC ATCCCAACCT      20

(2) INFORMATION FOR SEQ ID NO:4:

(i) SEQUENCE CHARACTERISTICS:
      (A) LENGTH: 20 Base pairs
      (B) TYPE: Nucleic acid
      (C) STRANDEDNESS: Single stranded
      (D) TOPOLOGY: Linear

```
(xi) SEQUENCE DESCRIPTION: SEQ ID NO:4:

CTTGACGAGT TCTTCTGAGG                                                                    20
```